United States Patent
Kakehi et al.

(10) Patent No.: US 8,691,795 B2
(45) Date of Patent: Apr. 8, 2014

(54) PROCESS FOR PRODUCING SUGAR CHAIN DERIVATIVE, STRUCTURE ANALYSIS METHOD, AND SUGAR CHAIN DERIVATIVE

(71) Applicant: Oksuka Chemical Co., Ltd., Tokushima (JP)

(72) Inventors: Kazuaki Kakehi, Nara (JP); Mitsuhiro Kinoshita, Osaka (JP); Yuki Matsuno, Osaka (JP)

(73) Assignee: Glytech, Inc., Kyoto (JP)

( * ) Notice: Subject to any disclaimer, the term of this patent is extended or adjusted under 35 U.S.C. 154(b) by 0 days.

(21) Appl. No.: 13/682,494

(22) Filed: Nov. 20, 2012

(65) Prior Publication Data

US 2013/0074585 A1    Mar. 28, 2013

Related U.S. Application Data

(62) Division of application No. 11/989,012, filed as application No. PCT/JP2006/314712 on Jul. 19, 2006, now Pat. No. 8,318,694.

(30) Foreign Application Priority Data

Jul. 19, 2005   (JP) ................. 2005-209077

(51) Int. Cl.
*A61K 31/715*   (2006.01)
*A61K 31/70*    (2006.01)
*C12Q 1/34*     (2006.01)
*A61K 35/12*    (2006.01)

(52) U.S. Cl.
USPC ............... 514/54; 514/23; 425/18; 435/18; 424/520

(58) Field of Classification Search
None
See application file for complete search history.

(56) References Cited

FOREIGN PATENT DOCUMENTS

JP    4-243898 A    8/1992

OTHER PUBLICATIONS

Otake et al. (2001) J. Biochem. 129, 537-542.*
Kitagawa et al. (1991) Biochem. Biophys. Res. Comm. vol. 178, No. 3, pp. 1429-1436.*
Savage, Angela, et al., "Structural Studies on the Major Oligosaccharides in a Variant Surface Glycoprotein of *Trypanosoma congolense*"; Molecular and Biochemical Parasitology, vol. 11 (1984); pp. 309-328.
Official Action dated Nov. 4, 2013, issued by the Taiwan Patent Office in related Taiwan Patent Application No. 100107065, with English translation (8 pages).
Van Pelt, Johannes, et al., "Storage of sialic acid-containing carbohydrates in the placenta of a human galactosialidosis fetus (Isolation and structural characterization of 16 sialyloligosaccharides)"; Eur. J. Biochem. vol. 177 (Feb. 1988); pp. 327-338. [Previsouly cited and considered in the Parent U.S. Appl. No. 11/989,012.].
Michalski, Jean Claude, et al., "Primary Structure of Three Mannosyl-glycoasparagines and Nine Sialyl-oligosaccharides Isolated from the rine of Two Patients with Gaucher's Disease (Infantile Form)"; Eur. J. Biochem. vol. 132 (Feb. 1983); pp. 375-381. [Previsouly cited and considered in the Parent U.S. Appl. No. 11/989,012.].
Official Action isued Sep. 3, 2013, by the Japan Patent Office in related Japanese Patent Application No. 2012-077958 (4 pages).
Herlant-Peers, Marie-Claire, et al., "Structure of Fifteen Oligosaccharides Isolated from New-Born Meconium"; Eur. J. Biochem., vol. 117, Feb. 1981; pp. 291-300.
Van Pelt, Johannes, et al., "Isolation and Structural Characterization of Twenty-One Sialyloligosaccharides from Galactosialidosis Urine"; Biol. Chem. Hoppe-Seyler, vol. 370, Mar. 1989; pp. 191-203.

* cited by examiner

*Primary Examiner* — Christopher R Tate
*Assistant Examiner* — Russell Fiebig
(74) *Attorney, Agent, or Firm* — Osha Liang LLP

(57) ABSTRACT

A process for preparing an oligosaccharide derivative from an oligosaccharide mixture, the process being characterized in that the process comprises the steps of (a) introducing a lipophilic group into oligosaccharides of the mixture to obtain a mixture of oligosaccharide derivatives, and (b) treating the oligosaccharide derivative mixture by serotonin affinity column chromatography.

3 Claims, 9 Drawing Sheets

PROCESS FOR PRODUCING SUGAR CHAIN DERIVATIVE, STRUCTURE ANALYSIS METHOD, AND SUGAR CHAIN DERIVATIVE

This application is a divisional of U.S. patent application Ser. No. 11/989,012, filed Apr. 22, 2009, which is a national stage application of PCT/JP/2006/314712, filed Jul. 19, 2006, which claims priority of Japanese Patent Application No. 2005-209077, filed Jul. 19, 2005. This application claims the priorities and benefits of these prior applications and incorporates these prior applications by reference in their entirety.

TECHNICAL FIELD

The present invention relates to a process for preparing oligosaccharide derivatives from a mixture of oligosaccharides and a method of analyzing the structure of oligosaccharides. The invention also relates to novel oligosaccharide derivatives produced by the process of the invention for preparing oligosaccharide derivatives.

BACKGROUND ART

It has been thought that oligosaccharides in glycoproteins have the functions, for example, of retaining the stereo structure of the protein and acquiring resistance for preventing the protein from decomposing with proteases. It has recently been revealed that oligosaccharides in glycoproteins participate in the phenomena of life such as fertilization and differentiation, signal transmission, canceration, intracellular transport of proteins and control of physiological activity. The clarification of the relationship between the bonding molecules on the surface of cells, glycoproteinaceous hormones and like oligosaccharides and the functions thereof has matured to the concept of glycoscience consortium. While the functional research on oligosaccharides has presently been conducted chiefly on sugar transferases (oligosaccharide genes) for effecting biosynthesis of oligosaccharides, sugar transferases are also preserved by genome information and participate in the functions of life through cooperation with other proteins. From this viewpoint, it is necessary to conduct functional analysis of oligosaccharides through structural glycomics procedures for capturing and analyzing the overall picture of oligosaccharides developing in the cells and tissues.

The structural glycomics in glycoscience functions to comprehensively analyze the oligosaccharide recognition mechanism which plays an important role in many phenomena of life, and this function is an indispensable element in functional glycomics. The technical factors required of structural glycomics are high comprehensiveness, high throughput, high sensitivity and high precision.

The structure of oligosaccharides in glycoprotein is presently analyzed by labeling oligosaccharides cut out from a protein with a fluorescent material and thereafter analyzing the oligosaccharides by high performance liquid chromatography (HPLC) and mass spectrometry (MS). This process has become useful means owing to a dramatic advance in mass spectrometry (Nonpatent Literature 1 to 4), and anion exchange column chromatography has been exclusively used for separating sialo oligosaccharides (Nonpatent Literature 5).

[Nonpatent Literature 1] Biomed Chromatogr. 16:103-115 (2002)
[Nonpatent Literature 2] Anal Biochem. 206: 278-287(1992)
[Nonpatent Literature 3] Biochem Soc Trans. 21:121-125 (1993)
[Nonpatent Literature 4] Chem Rev. 102: 321-369(2002)
[Nonpatent Literature 5] Biochim Biophys Acta. 705: 167-173(1982)

However, the comprehensive analysis of oligosaccharides in cells and tissues involves the problem of the versatility in the modification of the nonreducing terminal of sialic acid, fucose or the like and the branching of the oligosaccharide, so that it is impossible to fully separate the oligosaccharides which are present conjointly and to obtain a satisfactory result. Especially, the ion exchange column, which has no specific separating function, not only fails to effect full separation but also requires desalting treatment subsequent to the separation procedure, and is therefore not practically useful.

Accordingly, it has been earnestly desired to provide a useful method which is capable of fully analyzing the structure of oligosaccharides which is specific to particular cells or tissues, with consideration given to the nonuniformity in the information as to such oligosaccharides.

An object of the present invention is to provide means for individually separating and obtaining oligosaccharides from a mixture thereof like those present in cells or tissues.

Another object of the invention is to provide means for analyzing the structure of each oligosaccharide compound separated off.

Still another object of the invention is to provide novel oligosaccharide derivatives.

DISCLOSURE OF THE INVENTION

The present invention provides the following.

1. A process for preparing an oligosaccharide derivative from an oligosaccharide mixture, the process being characterized in that the process comprises the steps of (a) introducing a lipophilic group into oligosaccharides of the mixture to obtain a mixture of oligosaccharide derivatives, and (b) treating the oligosaccharide derivative mixture by serotonin affinity column chromatography.

2. A process for preparing an oligosaccharide derivative described above wherein the step (b) is followed by the step (c) of conducting normal phase chromatography with use of an amino column or amide column.

3. A process for preparing an oligosaccharide derivative described above wherein the step (c) is preceded by the step (d) of treating the resulting eluate with a glycosidase.

4. A method of analyzing the structure of an oligosaccharide in an oligosaccharide mixture, the process being characterized in that the process comprises the steps of (a) introducing a lipophilic group into oligosaccharides of the mixture to obtain a mixture of oligosaccharide derivatives, (b) treating the oligosaccharide derivative mixture by serotonin affinity column chromatography, and (e) treating the resulting eluate by a mass spectrometric method.

5. A method of analyzing the structure of an oligosaccharide described above wherein the step (b) is followed by the step (c) of conducting normal phase chromatography with use of an amino column or amide column.

6. A method of analyzing the structure of an oligosaccharide described above wherein the step (c) is preceded by the step (d) of treating the resulting eluate with a glycosidase.

7. A method of analyzing the structure of an oligosaccharide according to par. 4 wherein the mass spectrometric method comprise MALDI-TOF MS.

8. Oligosaccharide derivatives of the formulae (1) to (6) given below wherein $R^1$ is 2-caboxyphenyl, 3-carboxyphenyl, 4-carboxyphenyl, p-ethoxycarbonylphenyl or 2-pyridyl, $R^2$ is hydroxyl, the group -Asn or the group -Asn-$R^3$ wherein Asn is an asparagine group, $R^3$ is a carbamate-type or amide-type protective group, and Ac is acetyl.

9. A cancer marker derived from an oligosaccharide derivative of one of the formulae (1) to (6).

We have conducted intensive research and treated oligosaccharides by introducing a liophilic group into the oligosaccharides to obtain oligosaccharide derivatives, and subjecting the derivatives to affinity column chromatography wherein serotonin having affinity for sialic acid serves as a ligand. Consequently, we have found that asialo oligosaccharides can be separated from sialo oligosaccharides by this treatment, and that the sialo oligosaccharides can be separated further into monosialo, disialo, trisialo and tetrasialo oligosaccharides according to the number of sialic acid residues.

We have further found that when the fractions obtained by the affinity column chromatography are subjected to chromatography using an amino column or amide column, oligosaccharides which are different in branched structure can be obtained as separated meticulously. This makes it possible to produce a large quantity of oligosaccharide of single structure.

We have further found that when the oligosaccharide derivatives separated off are treated by causing a suitable glycosidase to act on each derivative, subjecting the reaction mixture to chromatography using an amino column or amide column for isolation and subjecting the resulting oligosaccharide derivative to mass spectrometry, the structure of oligosaccharides can be analyzed comprehensively with high precision. Thus the present invention has been accomplished.

The oligosaccharides of the oligosaccharide mixture to be used in the preparation process are not limited particularly but include asparagine-linked oligosaccharides (N-glycoside-linked oligosaccharides), mucin-type oligosaccharides (O-glycoside-linked oligosaccharides), free-type oligosaccharides and further oligosaccharides having an amino acid attached thereto, such as oligosaccharide-linked asparagine.

These oligosaccharides may be those prepared by a chemical method. For example oligosaccharides derived from natural glycoproteins are in the form of a mixture of oligosaccharides which are randomly deficient in the sugar residue at the nonreducing terminal, preferable to use is a mixture of such oligosaccharides. Also preferable to use is an oligosaccharide mixture including oligosaccharides having a sialic acid residue.

Examples of mixtures of oligosaccharides are oligosaccharide mixtures derived from natural materials such as milks, bovine-derived fetuin, eggs, or cells and tissues of living bodies. It is especially desirable to use oligosaccharides derived from cancer tissues or cancer cells since results of great interest are then expectable.

Examples of preferred mixtures of natural oligosaccharides are those given below, among which oligosaccharide mixtures including sialo oligosaccharides are desirable.

It is possible to use a mixture of oligosaccharide-linked asparagines which is prepared by obtaining a mixture of glycoproteins and/or glycopeptides from a natural material by a known method, causing a protease or the like to act on the mixture to cut off peptide portions and purifying the cut-off portions by chromatography with use of a gel filtration column or ion exchange column.

It is also possible to use a mixture of oligosaccharides which is obtained by homogenizing tissues or cells in an incubation medium using tissues or cells of a living body or incubated tissues or incubated cells, centrifuging the homogenized mixture to obtain a cell membrane fraction, treating the fraction with 2-mercaptoethyl alcohol and thereafter causing N-glycanase to act on the resulting fraction.

It is further possible to use a mixture of free oligosaccharides which is obtained by homogenizing incubated tissues or incubated cells, centrifuging the homogenized mixture and collecting the resulting supernatant. These oligosaccharides include neutral oligosaccharides, i.e., high mannose-type oligosaccharides or a wide variety of sialo oligosaccharides and are therefore suitable for use in preparing various oligosaccharides.

A lipophilic group is introduced into the oligosaccharides in the oligosaccharide mixture to obtain a mixture of oligosaccharide derivatives.

The lipophilic group is a substituent capable of dissolving lipids or soluble therein and to be formed by reacting with a ring-opened aldehyde at the reducing terminal of the oligosaccharide, or with the asparagineamino group or carboxyl group of the oligosaccharide-linked asparagine. Examples of such substituents are those usually useful as fluorescent labels, such as 2-, 3- or 4-carboxyphenylamino group, p-ethoxycarbonylphenylamino group and 2-pyridylamino group, and substituents for use as carbamate-type or amide-type protective groups, such as 9-fluorenylmethoxycarbonyl (Fmoc) group, tert-butoxycarbonyl (BOC) group, benzyl, allyl, allyloxycarbonyl and acetyl.

These lipophilic groups can be introduced into oligosaccharides by a known method. Preferable to use is 2-carboxyphenylamino group, Fmoc group or BOC group in view of ease of handling and the stability of the oligosaccharide to be obtained, and because the excitation light corresponds to a mercury light source or laser light source.

For example, an aminoalditol derivative can be prepared by reacting 2-aminobenzoic acid with an oligosaccharide in the presence of a reducing agent such as sodium cyanoborohydride or (dimethylamino)borane.

Further for example, 9-fluorenylmethyl-N-succinimidyl carbonate can be reacted with oligosaccharide asparagine in the presence of sodium hydrogencarbonate, whereby Fmoc group can be introduced into the asparagine, as attached to the amino group of the asparagine in the manner of carbamate.

The procedures described above afford mixtures of oligosaccharide derivatives having a lipophilic group introduced therein.

The mixture of oligosaccharide derivatives obtained is subjected to serotonin affinity column chromatography for separation.

An affinity column wherein serotonin having affinity for sialic acid serves as a ligand is used for the serotonin affinity chromatography to be conducted in the present invention.

The serotonin affinity column may be prepared by immobilizing serotonin to a filler material, or a column commercially available may be used. An example of commercial column is LA-Serotonin Column (product of J-OIL MILLS, INC.). The separation conditions for chromatography are suitably determined. For example, linear gradient elution can be conducted for separation using a fluorescent detector at an excitation wavelength of 350 nm, fluorescent wavelength of 425 nm and flow rate of 0.5 ml/min, and using a mobile phase comprising ultrapure water and aqueous solution of ammonium acetate.

The mixture of oligosaccharide derivatives can be separated according to the number of sialic acid residues in the oligosaccharide derivatives. First eluted are asialo oligosaccharide derivatives having no sialic acid residues, subsequently eluted are monosialo oligosaccharide derivatives and thereafter eluted are disialo derivatives. Thus eluates are separately obtained in proportion to the increase in the number of sialic acid residues.

The oligosaccharide derivatives thus separated by the serotonin affinity column are treated by normal phase HPLC using a polymer-base amino column or silica-base amide column, whereby the oligosaccharide derivatives can be separated from one another meticulously. The term "normal phase chromatography" refers to a chromatographic procedure wherein a polar solid phase of amino group, aminopropyl group or acrylamide group is used as the filling material. This procedure is characterized by the separation effected based on the difference in the degree of distribution of the sample components to the solid phase and mobile phase. Basically this mode of separation is based on the hydrophilic properties of oligosaccharides. This mode of chromatography is usable favorably also for the separation of isomers of oligosaccharides having sialic acid attached thereto. The procedure is usable also favorably for the separation of asialo oligosaccharides which are treated with a dilute acid or neuraminidase.

The polymer-base amino column to be used may be a column prepared by the user and filled with a stationary phase which comprises a polymer, such as polyvinyl alcohol-base polymer gel, having amino group attached thereto, whereas a commercial column is usable.

The amino column commercially available is, for example, Asahi Shodex NH2P-504E (product of Showa Denko K.K.). An example of commercial amide column is TSK-GEL Amide-80 (product of TOSOH Corp.).

The separation conditions for chromatography are suitably determined. For example, linear gradient elution can be conducted for separation using a fluorescent detector at an excitation wavelength of 350 nm, fluorescent wavelength of 425 nm and flow rate of 1 ml/min, and using a mobile phase comprising acetonitrile containing acetic acid and aqueous solution containing acetic acid and triethylamine.

The oligosaccharide structure of the oligosaccharide derivative thus obtained by isolation can be analyzed by the application of glycosidase and mass spectrometry.

The glycosidase to be used can be a known one. Examples of such enzymes usable are sialidase, galactosidase, mannosidase, N-acetylglucosamidase, fucosidase, etc.

The mass spectrometry can be conducted by a mass spectrometer for practicing a conventional known mass spectrometric method. The measurement may preferably be conducted by MALDI-TOF MS that is used especially for oligosaccharide analysis in recent years.

The structure of oligosaccharides is analyzed by causing a specified glycosidase to act on the oligosaccharide, thereafter treating the reaction mixture by normal phase HPLC using a polymer-base amino column or a silica-base amide column, subjecting the resulting fraction to mass spectrometry with consideration given to a loss of mass and characteristics of hydrolase, and repeating these steps.

The lipophilic group is removed from the oligosaccharide derivative obtained. In this way, various oligosaccharides can be artificially obtained easily in large quantities.

The lipophilic group can be removed by a conventional known method.

For example, 2-carboxyphenylamino group can be removed by reacting hydrogen peroxide with the oligosaccharide derivative in acetic acid at room temperature, whereby a free-type oligosaccharide can be collected easily.

Fmoc group is removable by reacting morpholine with the oligosaccharide derivative in N,N-dimethylformamide. BOC group is removable by reacting a weak acid with the oligosaccharide derivative.

In the case where the oligosaccharide is oligosaccharide-linked asparagine, the asparagine residue is removable, for example, by reacting anhydrous hydrazine with the asparagine and thereafter acetylating the reaction mixture, or by refluxing the asparagine in a basic aqueous solution with heating and thereafter acetylating the reaction mixture.

Such oligosaccharides are very useful in the field of developing pharmaceuticals. For example, these oligosaccharides are useful for the synthesis of cancer vaccines. The oligosaccharide obtained may be subjected to a combination of chemical reactions and reactions with sugar transferases and thereby made into a derivative wherein new sugar residues are added to the oligosaccharide for the development of a novel vaccine.

The structure analyzing method and the preparation process of the present invention have made it possible for us to isolate the oligosaccharides of the formulae (1) to (6) given below which have not been found in various cancer cells.

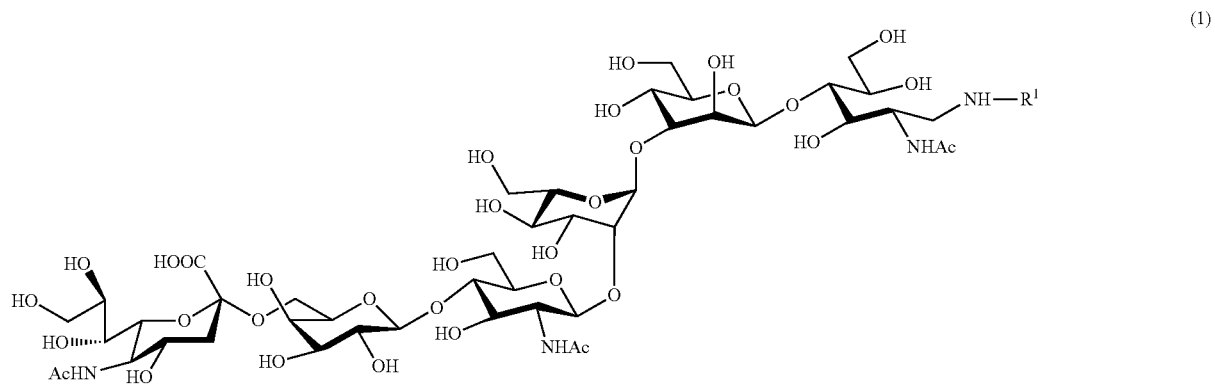

(1)

-continued
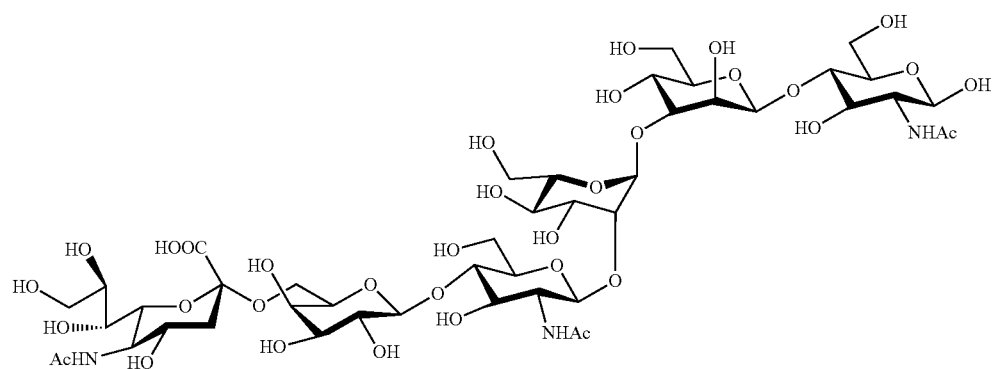
(2)
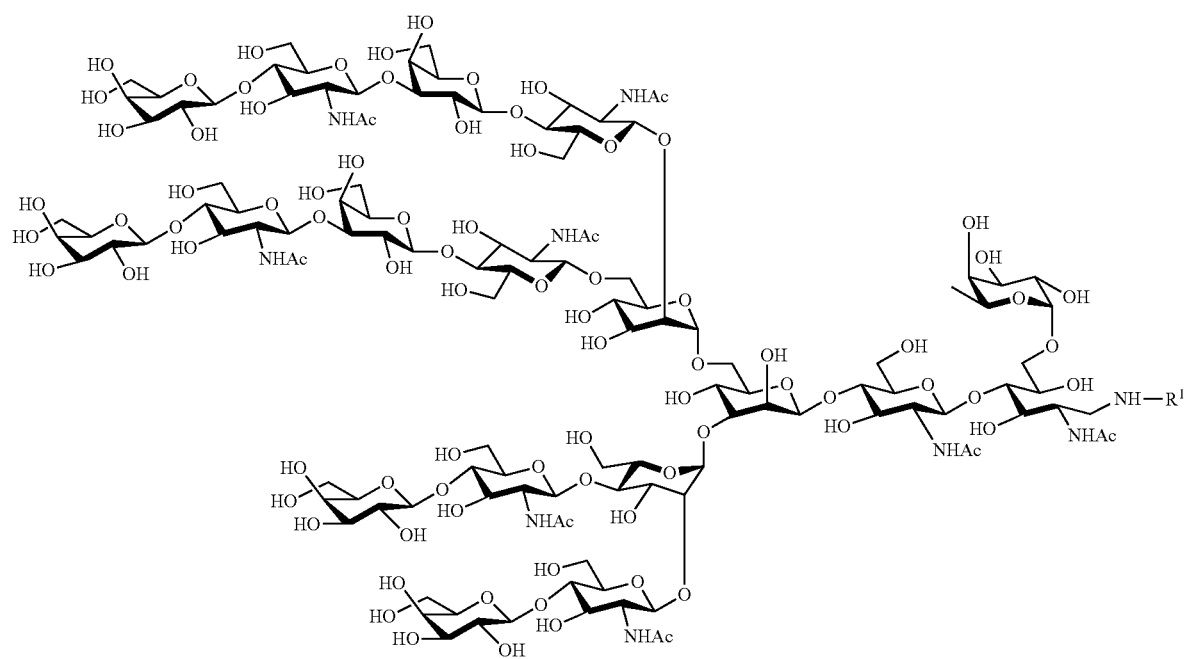
(3)
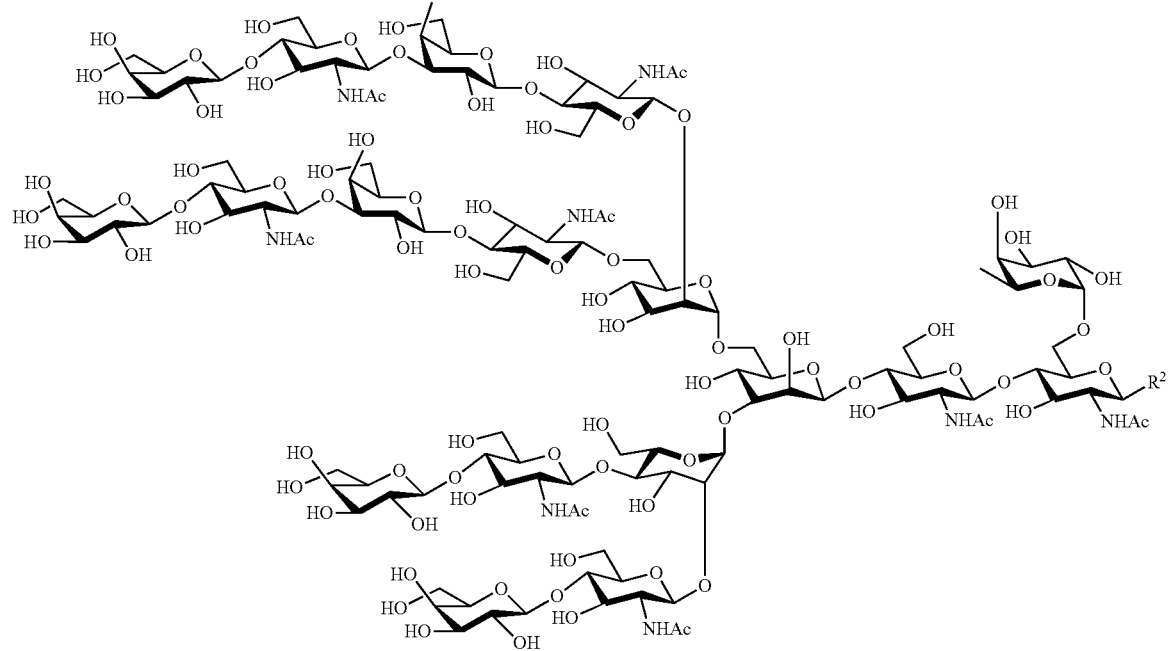
(4)

-continued

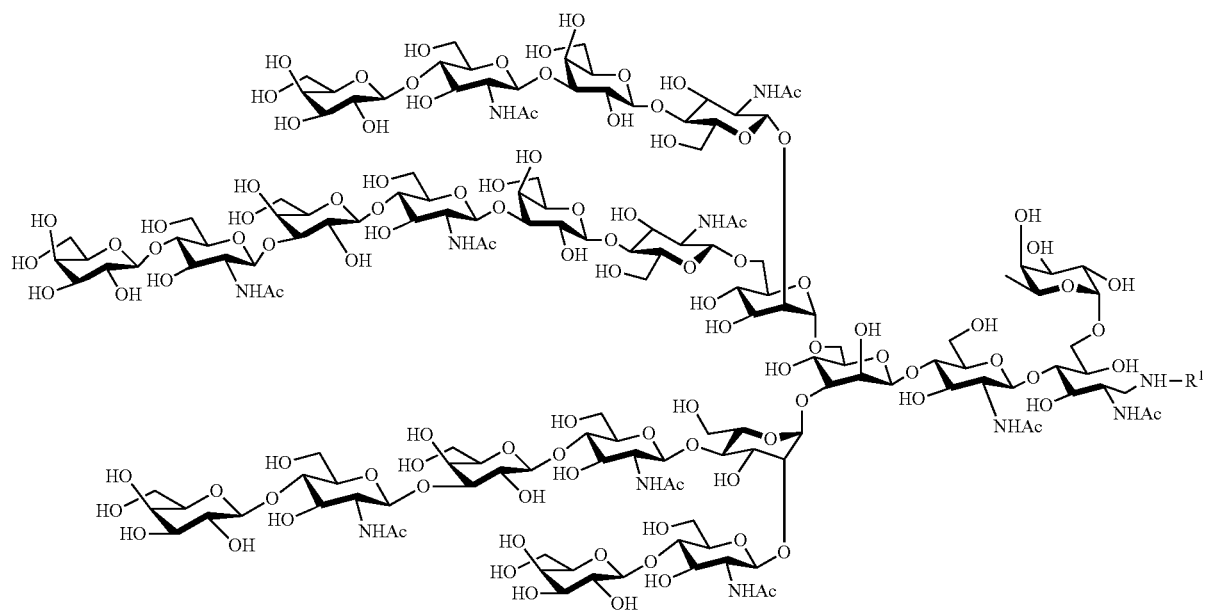

(5)

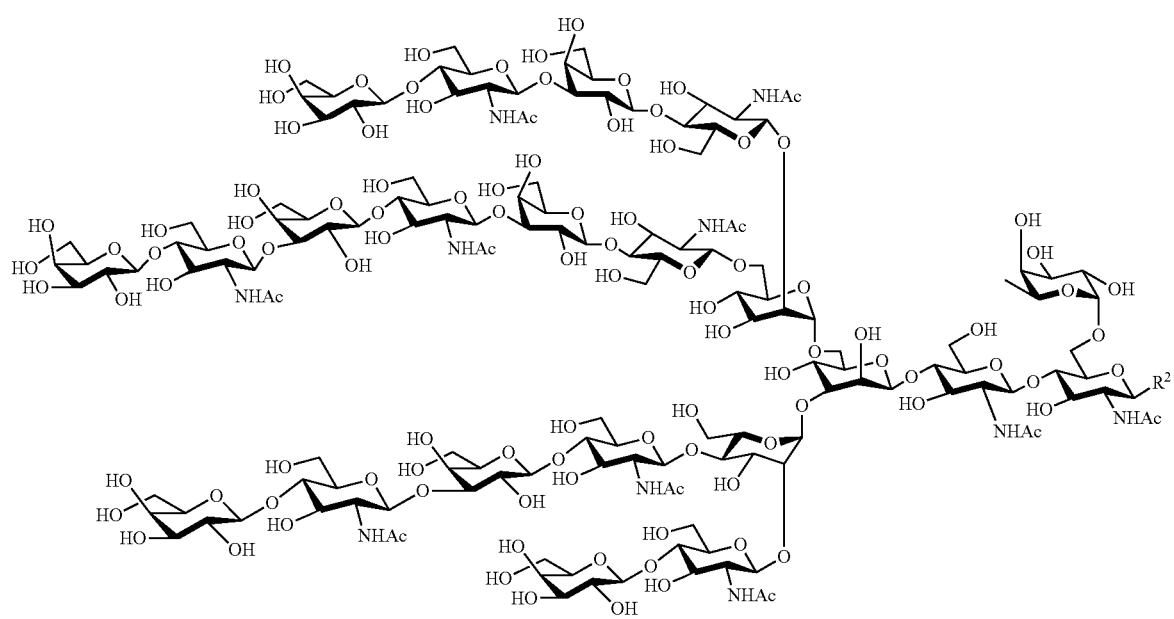

(6)

wherein $R^1$ is 2-caboxyphenyl, 3-carboxyphenyl, 4-carboxyphenyl, p-ethoxycarbonylphenyl or 2-pyridyl, $R^2$ is hydroxyl, the group -Asn or the group -Asn-$R^3$ wherein Asn is an asparagine group, $R^3$ is a carbamate-type or amide-type protective group, and Ac is acetyl.

It is thought that these novel oligosaccharides appear specifically in cancer cells, and such oligosaccharides can be utilized as cancer markers.

For example, a polyclonal antibody or monoclonal antibody is prepareed which specifically recognizes a specific oligosaccharide in cancer cells, for use in detecting the oligosaccharide by an immunological technique.

For the preparation of polyclonal antibody, the oligosaccharide or a hapten thereof is combined with a protein or like high molecular compound (carrier) to serve as an antigen, which is used to immunologically sensitize a mammal, such as mouse, hamster, guinea pig, chicken, rat, rabbit, canine, goat, sheep or bovine, and blood is collected from the mammal to obtain an antiserum containing a polyclonal antibody.

A hybridoma which is obtained by the fusion, for example, of antibody-producing cells and myeloma cell strain is incubated to produce a monoclonal antibody, which is then purified.

BEST MODE OF CARRYING OUT THE INVENTION

Reference Examples and Examples are given below. However, the invention is not limited to the examples given below.

Example 1

Separation of Human Serum-Derived [1-Acidic Glycoprotein (AGP)] Oligosaccharides by Serotonin Affinity Chromatography One mg of human serum-derived AGP (product of Sigma-Aldrich Japan) was dissolved in 50 µl of 20 mM phosphoric acid buffer solution (pH 7.5), N-glycanase F (2 units, 4 µl) was added to the solution, and the mixture was reacted at 37° C. for 12 hours. The resulting reaction mixture was boiled at 100° C. for 3 minutes and centrifuged, and the supernatant was collected.

To the collected supernatant was added 100 µl of a solution obtained by dissolving 2-aminobenzoic acid (2-AA) and sodium cyanoborohydride each to a concentration of 3% in a mixture (500 µl) of 2% of boric acid and 4% of sodium acetate, followed by a reaction at 80° C. for 1 hour. The reaction mixture was fractionated using a Sephadex LH-20 column (0.7 cm, i.d., 30 cm) as equilibrated with a 50% aqueous solution of methanol, the resulting fractions were measured using a spectrophotometer (product of Hitachi, Ltd., Model F-4010) at an excitation wavelength of 335 nm and fluorescent wavelength of 410 nm, and the fluorescent fraction eluted first was collected as a mixture of oligosaccharide derivatives.

Figure 1:
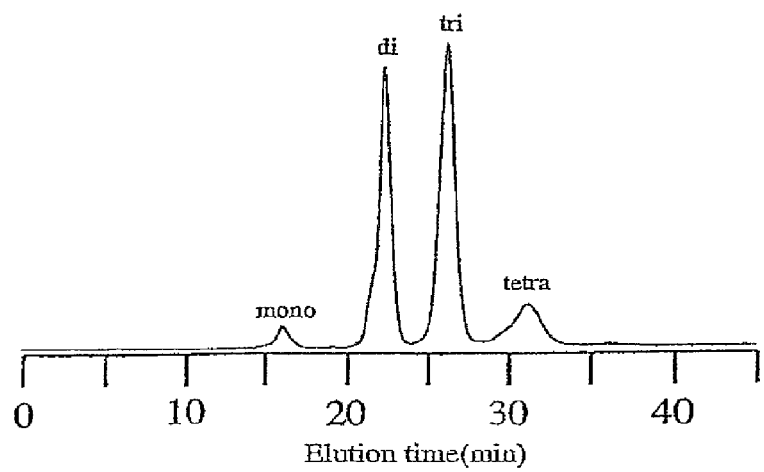
FIG. 1 is an affinity column chromatogram of oligosaccharide derivatives obtained in Example 1.

The mixture obtained was subjected to serotonin affinity column chromatography to obtain separated oligosaccharide derivatives. FIG. 1 shows the result of separation by the affinity column chromatography.

Conditions for serotonin affinity column chromatography
Column: LA-Serotonin column (4.6×150 mm, product of Japan Oil Mills)
Pump: JASCO Model PU-980
Flow rate: 0.5 ml/min
Detector: JASCO Model FP-920 fluorescent detector
Excitation wavelength: 350 nm
Fluorescent wavelength: 425 nm
Mobile phase: ultrapure water used as solution A, and 40 mM ammonium acetate aqueous solution as solution B Gradient conditions: Linear gradient elution was conducted using 5% of solution B for 2 minutes after the sample was poured in and using the ammonium acetate solution so that the concentration thereof would be 30 mM 37 minutes later and subsequently 40 mM 10 minutes later.

The same conditions as above were used in the following examples for separation by serotonin affinity chromatography.

Example 2

Separation of Human Cancer Cell-Derived Oligosaccharides by Serotonine Affinity Chromatography Cell Incubation Used for incubation were human renal adenocarcinoma cells ACHN, human lung cancer cells A549, human gastric cancer cells MKN45 and human cell lymphocytic lymphoma U937. Cells were incubated in cell cultivation dishes in the presence of 5% $CO_2$ at 37° C., using DMEM (Dulbecco's Modified Eagle Medium, product of Sigma-Aldrich Japan) containing 10% of bovine serum [newborn calf serum (NCS), product of Sigma-Aldrich Japan] as immobilized by being heated at 50° C. for 30 minutes in advance for ACHN and A549 and using RPMI-1640 (product of Sigma-Aldrich Japan) containing 10% of NCS for U837 and MKN45. The cells other than U937 were washed as held in an 80% confluent state with an isotonic phosphoric acid buffer (PBS) during cultivation and then treated at 37° C. for 5 minutes with addition of trypsin, and the cells separated off were collected, subsequently washed with PBS and thereafter subcultured.

Preparation of Cell Membrane Fraction

Cells in 80% confluent state for use in preparing a cell membrane fraction were collected from the incubator using a cell scraper. The cells collected were washed with PBS and homogenized with a glass homogenizer in 10 mM $Na_2HPO_4$ (pH 7.5) containing 1% protease inhibitor to a concentration of $1×10^5$ cells/5 ml, 10 ml of 20 mM Tris-HCl buffer (pH 7.5) containing 0.5 M sucrose was then added to the mixture, the resulting mixture was centrifuged at 3000 rpm, 4° C. for 15 minutes, and the supernatant was thereafter collected and centrifuged at 19000 rpm, 4° C. to obtain a precipitate as a cell membrane fraction.

Separation of Oligosaccharides from the Cell Membrane Fraction

Added to the cell membrane fraction ($1×10^7$ cells) were 40 µl of 1% SDS solution first and then 2-mercaptoethyl alcohol to a concentration of 1%, and the mixture was thereafter heated on a water bath boiling at 100° C. for 5 minutes for solubilization. The solution containing the membrane fraction was cooled to room temperature, NP-40 was added to a concentration of 1%, and phosphoric acid buffer (pH 7.5) was added to the mixture to a final concentration of 20 mM. With addition of 4 µl of N-glycanase F (2 units, product of Roche Diagnostics), the mixture was incubated at 37° C. overnight and boiled on a water bath boiling at 100° C. for 5 minutes, 95% ethanol was added to the mixture to a final concentration of 75%, the resulting mixture was centrifuged at 15000 rpm, 4° C., and the supernatant was treated in a vacuum to dryness to obtain oligosaccharides derived from the cell membranes.

Figure 2:
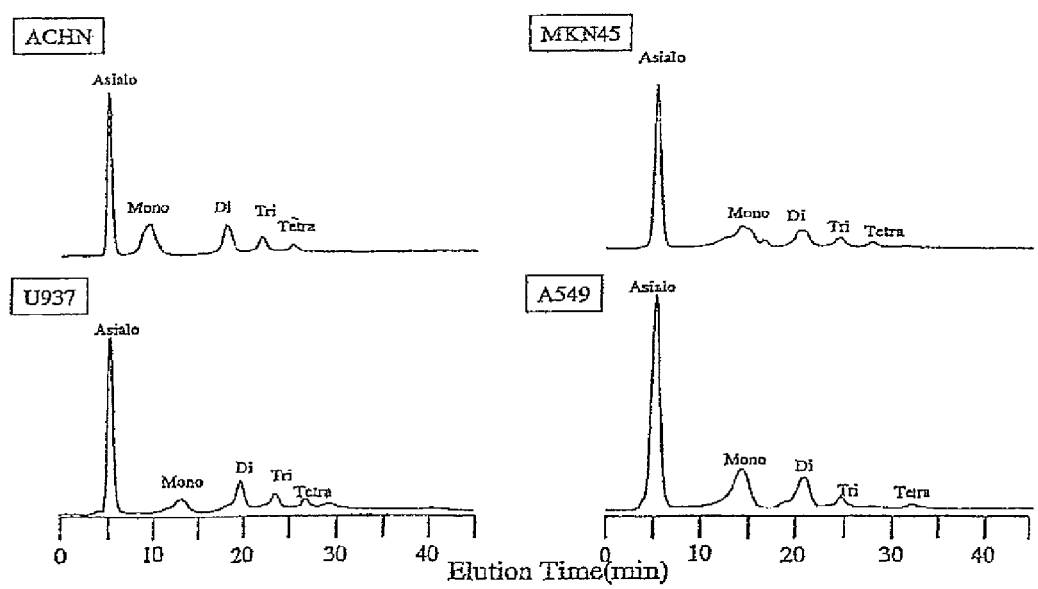
FIG. 2 are affinity column chromatograms of oligosaccharide derivatives obtained in Example 2.
Figure 3:
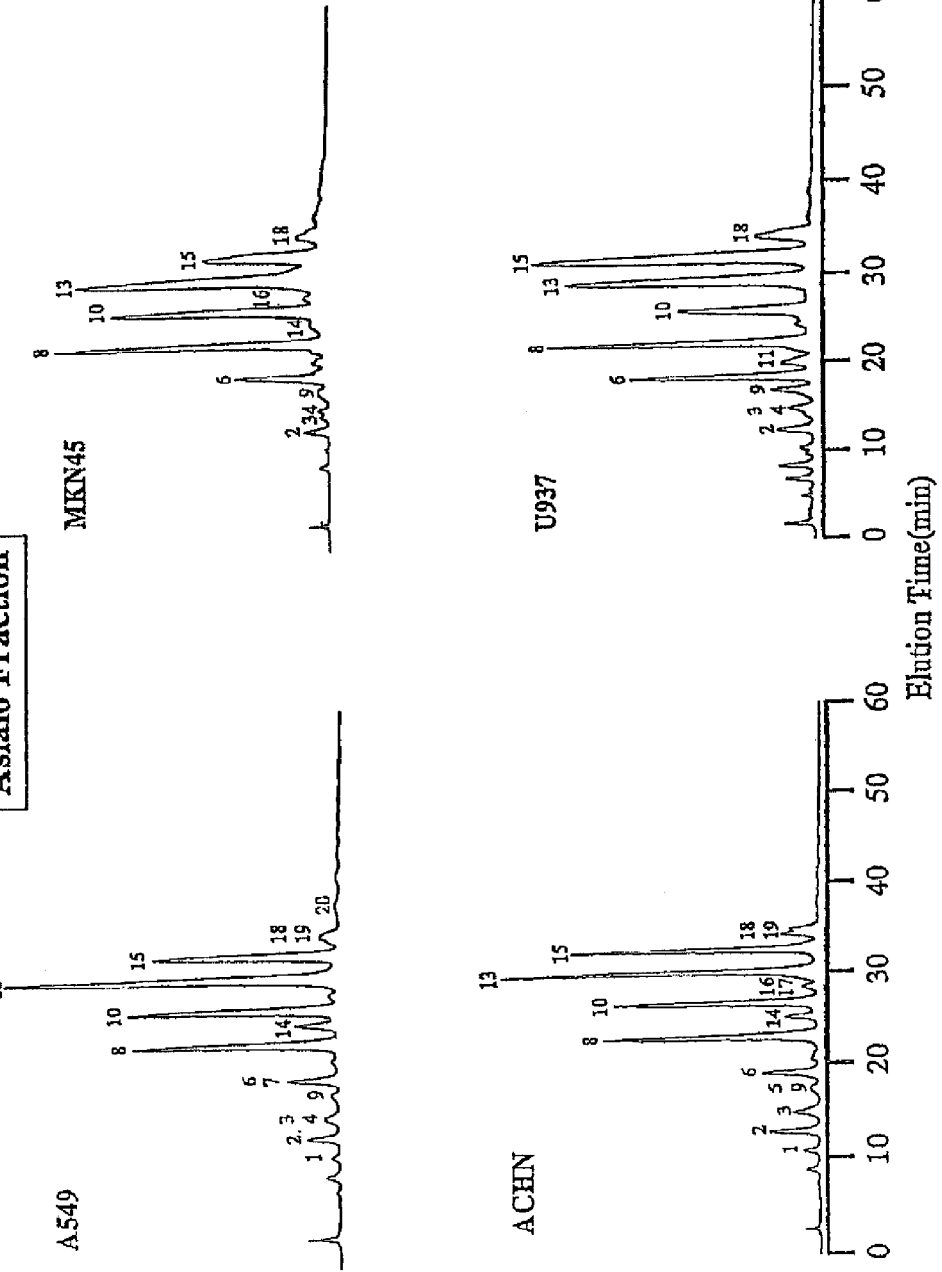
FIG. 3 are chromatograms of HPLC of oligosaccharide derivatives obtained in Example 3.
Figure 4:
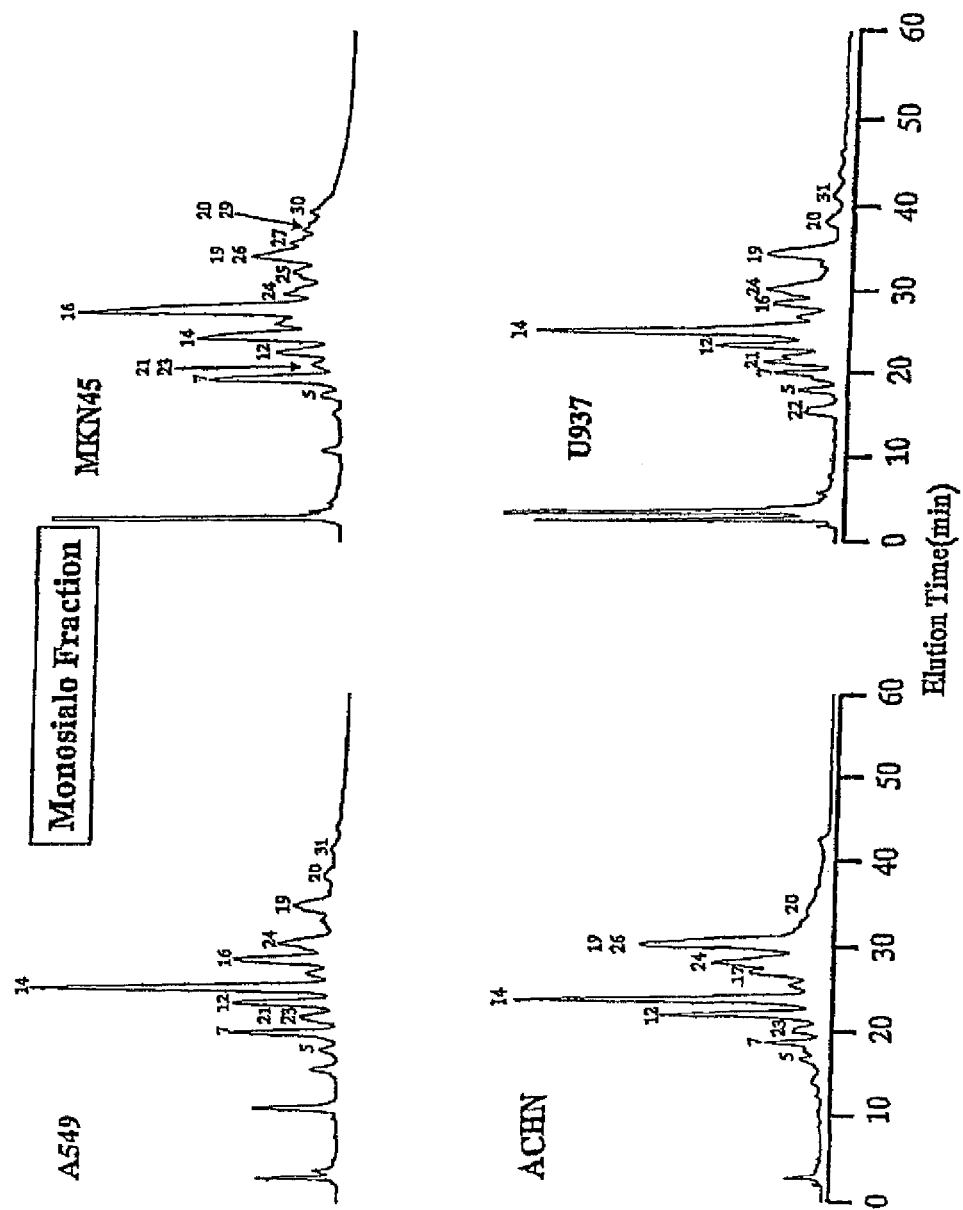
FIG. 4 are chromatograms of HPLC of oligosaccharide derivatives obtained in Example 3.
Figure 5:
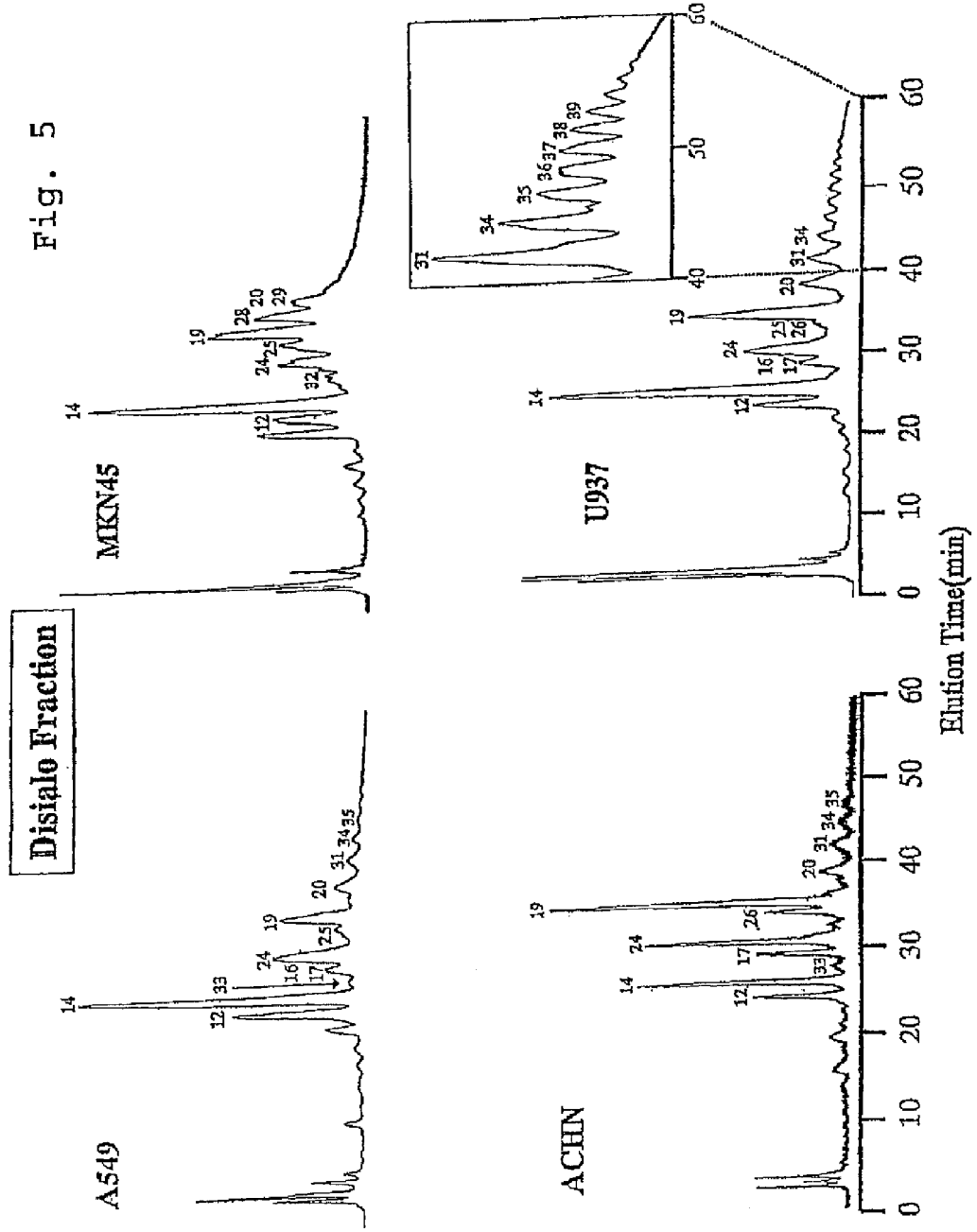
FIG. 5 are chromatograms of HPLC of oligosaccharide derivatives obtained in Example 3.
Figure 6:
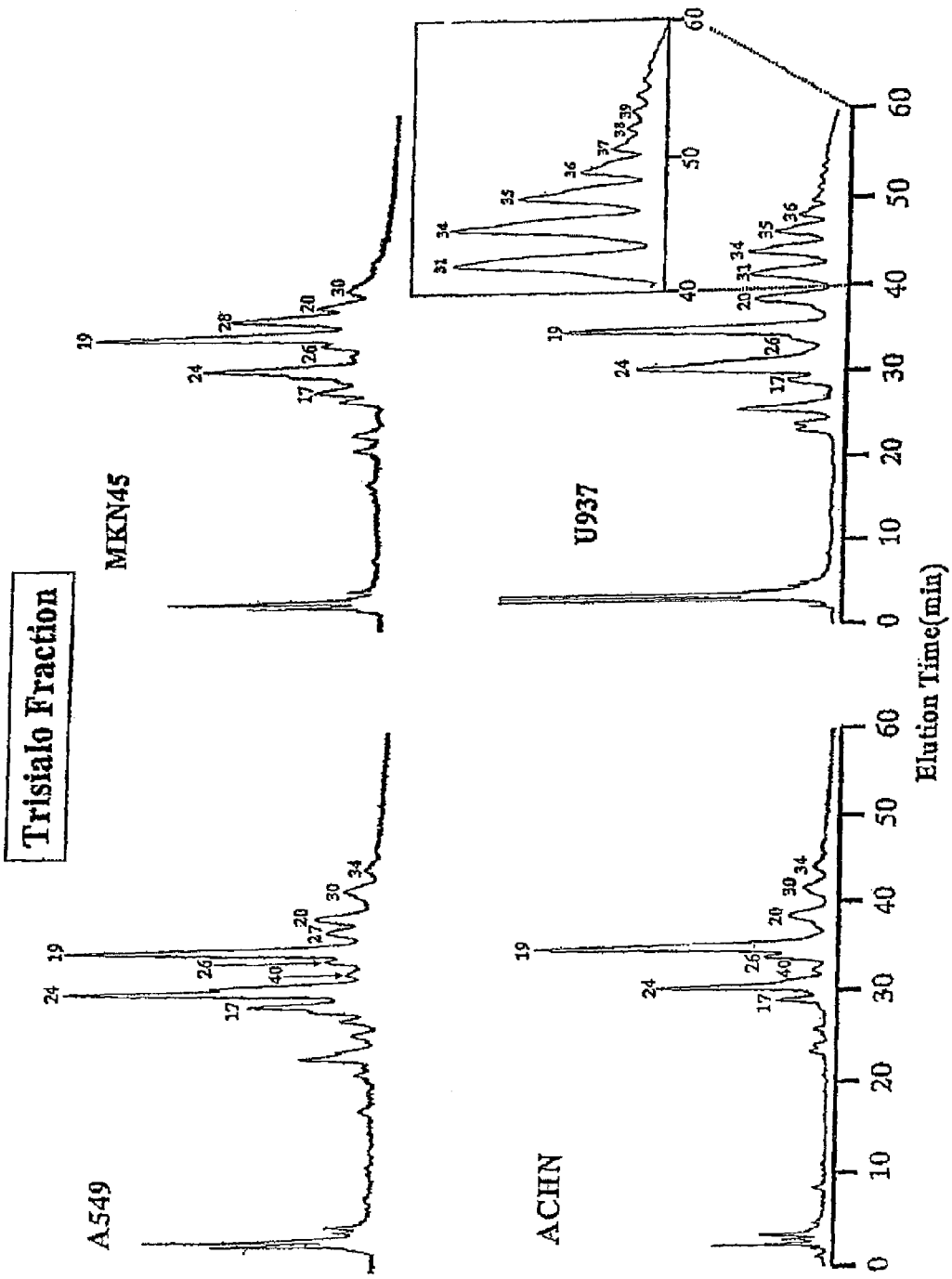
FIG. 6 are chromatograms of HPLC of oligosaccharide derivatives obtained in Example 3.
Figure 7:
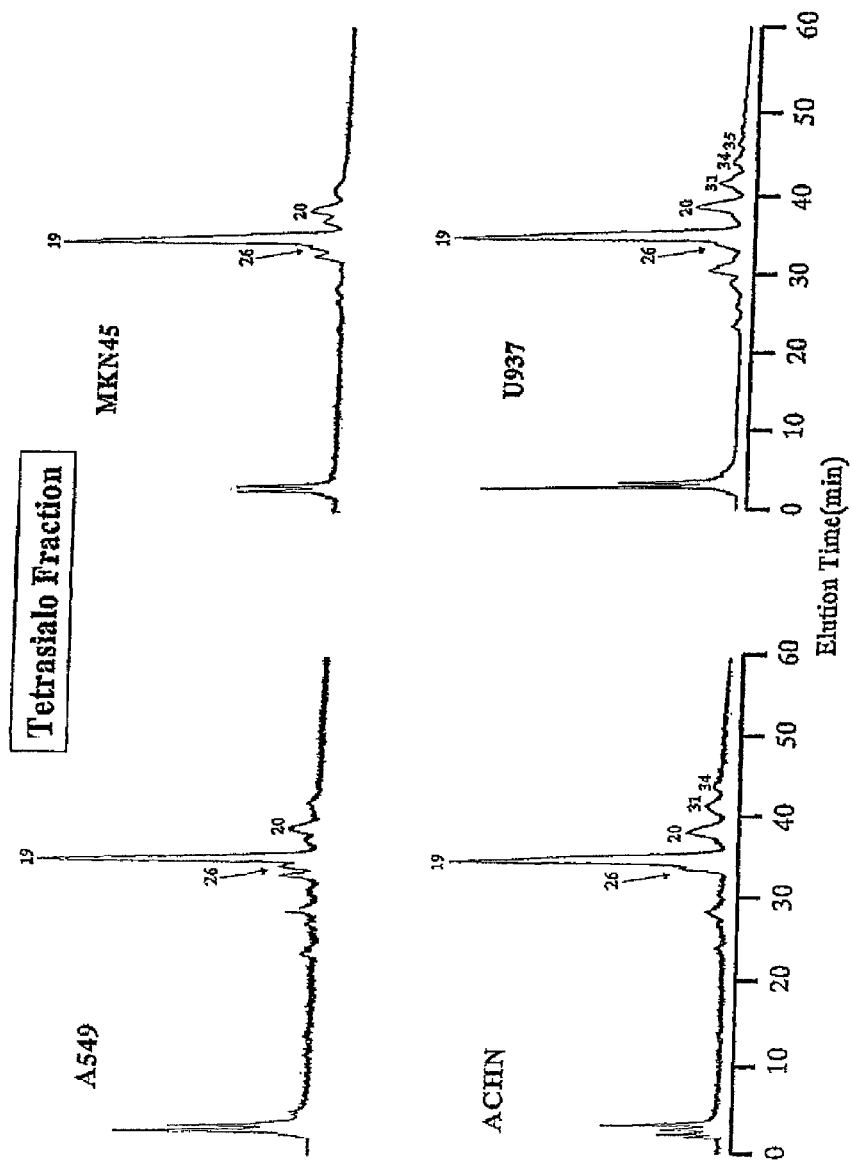
FIG. 7 are chromatograms of HPLC of oligosaccharide derivatives obtained in Example 3.

In the same manner as in Example 1, 2-AA was introduced into the oligosaccharides, followed by serotonin affinity column chromatography to obtain oligosaccharide fractions. FIG. 2 shows the result of separation by the column chromatography.

Example 3

Separation of Cancer Cell-Derived Oligosaccharides by Normal Phase Chromatography and Structural Analysis The cancer cell-derived oligosaccharide derivatives (corresponding to $1\times10^7$ cells) of each fraction obtained in Example 2 were dissolved in 20 μl of 20 mM acetic acid buffer (pH 5.0), 4 μl of sialidase (2 mU, product of Marukin Bio) was added to the solution, and the mixture was reaction at 37° C. for 24 hours. The reaction mixture was boiled at 100° C. for 3 minutes and centrifuged to obtain a supernatant.

The resulting supernatant was subjected to normal phase HPLC using an amide column to obtain oligosaccharide fractions. FIGS. 3 to 7 show the result of separation by HPLC.
Conditions for HPLC
Column: TSK-GEL Amide-80 (TOSOH CORPORATION, Japan, 4.6×250 mm)
Column temperature: 40° C.
Pump: JASCO Model PU-980
Flow rate: 1 ml/min
Detector: JASCO Model FP-920 fluorescent detector
Excitation wavelength: 350 nm
Fluorescent wavelength: 425 nm
Mobile phase: acetonitrile solution containing 0.2% acetic acid and serving as solution A and aqueous solution containing 0.1% of acetic acid and 0.1% of triethylamine and used as solution B
Gradient conditions: Linear gradient elution was conducted using 30% of solution B for 2 minutes after the sample was poured in so that the amount of solution B would be 65% in 60 minutes.

Glycosidase and Structural Analysis by Mass Spectrometry

The oligosaccharide derivative of peak 31 derived from U937 was dissolved in 20 μl of 20 mM citric acid buffer (pH 3.5), 1 μl of β-galactosidase (25 mU, product of Seikagaku Kogyo Co., Ltd) was added to the solution, and the mixture was reacted at 37° C. for 24 hours. The reaction mixture was boiled at 100° C. for 3 minutes and centrifuged to collect the supernatant. The supernatant obtained was subjected to normal phase HPLC using an amide column, affording a fraction, which was analyzed by MALDI-TOF MS. As a result, an oligosaccharide (a) was obtained which was 2718 in molecular weight.

The oligosaccharide derivative (a) obtained was dissolved in 20 μl of 20 mM citric acid buffer (pH 5.0), 1 μl of β-N-acetylhexaminidase (10 mU, product of Seikagaku Kogyo Co., Ltd) was added to the solution, and the mixture was reacted at 37° C. for 24 hours. The reaction mixture was boiled at 100° C. for 3 minutes and centrifuged to collect the supernatant. The supernatant obtained was analyzed in the same manner as above, affording an oligosaccharide derivative (b) which was 1906 in molecular weight.

The oligosaccharide derivative (b) was further treated with β-galactosidase, consequently affording an oligosaccharide derivative (c) which was 1582 in molecular weight.

These results revealed that the peak 31 was the oligosaccharide of the formula given below.

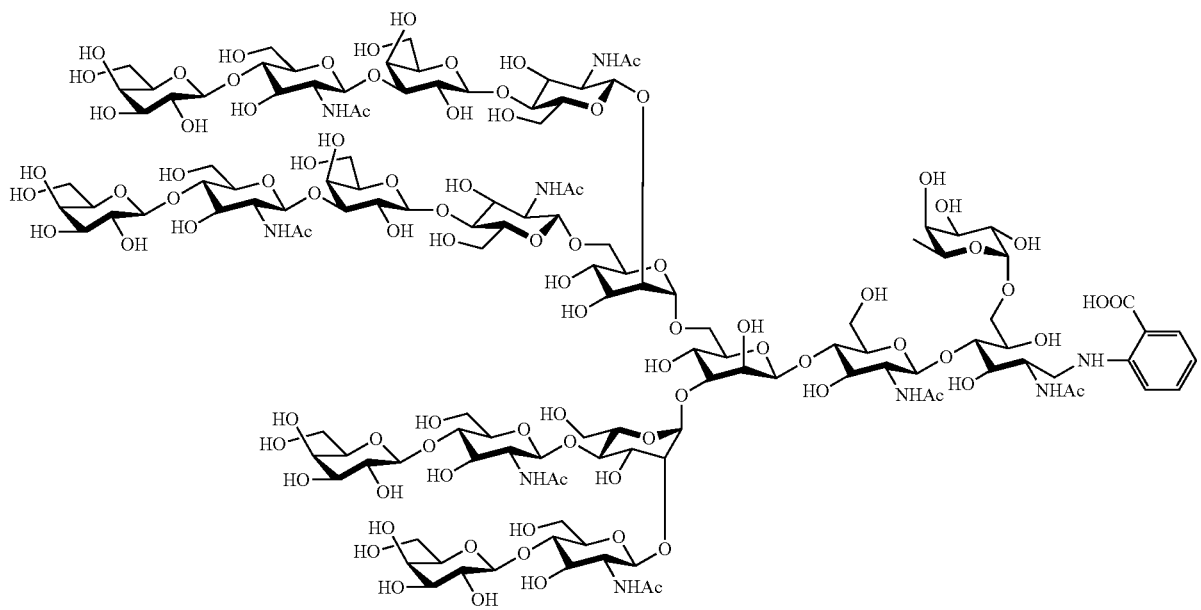

Similarly, the oligosaccharide derivative of peak 35 was treated with β-galactosidase, β-N-acetylhexaminidase and then with β-galactosidase, whereby the derivative was found to be the oligosaccharide of the formula given below.

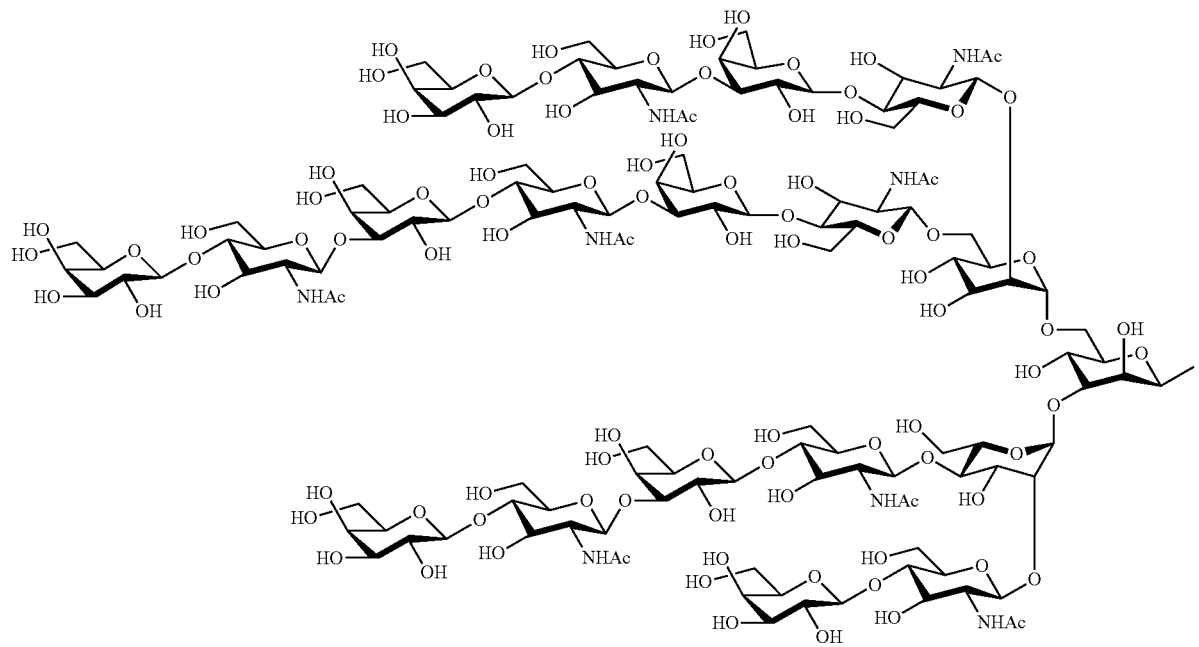

Using suitable hydrolases, MALDI-TOF MS was conducted for the derivatives of other peaks. Tables 1 to 5 show oligosaccharide structures corresponding to the peaks shown in FIGS. 3 to 7. The molecular weights given in Tables 1 to 14 are those (MW) of compounds wherein 2-aminobenzoic acid is attached to the reducing terminal of the oligosaccharide. The symbols resent the following.

Gal: D-galactose, GlcNAc: N-acetylglucosamine, Man: D-mannose, Fuc: fucose, 2-AA: 2-aminobenzoic acid, NeuAc: sialic acid.

The oligosaccharide wherein 2-aminobenzoic acid is attached to the reducing terminal thereof, for example, the structure of the oligosaccharide portion represented by the formula given below will be represented by -4GlcNAcβ1-4GlcNAc-2-AA.

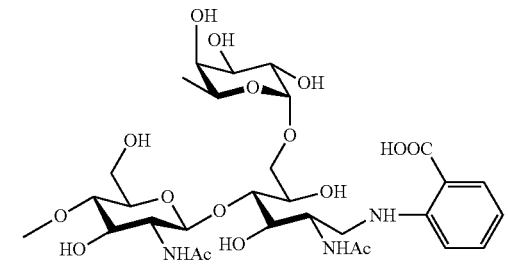

MALDI-TOF MS analysis

The device used was Voyager DE-PRO (PE Biosystems, Framingham, Mass.). The measurement was conducted in linear/negative ion mode at an acceleration voltage of 20 kV and grid voltage of 96.3% with a delay time of 1000 nsec, lens offset 1.25 and laser intensity (nitrogen laser) of 2700. A 0.5 μL quantity of the sample as dissolved in water was kneaded with 0.5 μL of 20 mg/mL methanol solution of 2,5-dihydroxybenzoic acid (DHB), and the mixture was dried to obtain a sample for use in measurement.

TABLE 1

| Peak No. | MW | Structure |
|---|---|---|
| 1 | 1029 | Manα1-6(Manα1-3)Manβ1-4GlcNAcβ1-4GlcNAc-2-AA |
| 2 | 1176 | Manα1-6(Manα1-3)Manβ1-4GlcNAcβ1-4GlcNAc(Fucα1-6)-2-AA |
| 3 | 1192 | Man-Manα1-6(Manα1-3)Manβ1-4GlcNAcβ1-4GlcNAc-2-AA |
| 4 | 1379 | Manα1-6(GlcNAc-Manα1-3)Manβ1-4GlcNAcβ1-4GlcNAc(Fucα1-6)-2-AA |
| 5 | 1395 | Manα1-6(Galβ1-4GlcNAc-Manα1-3)Manβ1-4GlcNAcβ1-4GlcNAc-2-AA |
| 6 | 1354 | Man(Man-Manα1-6)(Manα1-3)Manβ1-4GlcNAcβ1-4GlcNAc-2-AA |
| 7 | 1541 | Manα1-6(Galβ1-4GlcNAc-Manα1-3)Manβ1-4GlcNAcβ1-4GlcNAc(Fucα1-6)-2-AA |
| 8 | 1516 | Man(Man-Manα1-6)(Man-Manα1-3)Manβ1-4GlcNAcβ1-4GlcNAc-2-AA |
| 9 | 1582 | GlcNAc-Manα1-6(GlcNAc-Manα1-3)Manβ1-4GlcNAcβ1-4GlcNAc(Fucα1-6)-2-AA |
| 10 | 1678 | Man-Man(Man-Manα1-6)(Man-Manα1-3)Manβ1-4GlcNAcβ1-4GlcNAc-2-AA |
| 11 | 1785 | GlcNAc(GlcNAc-Manα1-6)(GlcNAc-Manα1-3)Manβ1-4GlcNAcβ1-4GlcNAc(Fucα1-6)-2-AA |

TABLE 2

| Peak No. | MW | Structure |
|---|---|---|
| 12 | 1760 | Galβ1-4GlcNAc-Manα1\6→Manβ1-4GlcNAcβ1-4GlcNAc-2-AA; Galβ1-4GlcNAc-Manα1/3 |
| 13 | 1840 | Man\Man-Man-Manα1\6→Manβ1-4GlcNAcβ1-4GlcNAc-2-AA; Man-Man-Manα1/3 |
| 14 | 1906 | Galβ1-4GlcNAc-Manα1\6→Manβ1-4GlcNAcβ1-4GlcNAc-2-AA; Galβ1-4GlcNAc-Manα1/3; Fucα1→6 |
| 15 | 2002 | Man-Man\Man-Man-Manα1\6→Manβ1-4GlcNAcβ1-4GlcNAc-2-AA; Man-Man-Manα1/3 |
| 16 | 2052 | Galβ1-4GlcNAc-Manα1\6→Manβ1-4GlcNAcβ1-4GlcNAc-2-AA; Galβ1-4GlcNAc-Manα1/3; Fucα1 (3-linked); Fucα1→6 |
| 17 | 2125 | Galβ1-4GlcNAc\Galβ1-4GlcNAc-Manα1\6→Manβ1-4GlcNAcβ1-4GlcNAc-2-AA; Galβ1-4GlcNAc-Manα1/3 |
| 18 | 2116 | GlcNAc\Galβ1-4GlcNAc-Manα1\6→Manβ1-4GlcNAcβ1-4GlcNAc-2-AA; Galβ1-4GlcNAc-Manα1/3,4; GlcNAcα1 |
| 19 | 2636 | Galβ1-4GlcNAc\Galβ1-4GlcNAc-Manα1\6→Manβ1-4GlcNAcβ1-4GlcNAc-2-AA; Galβ1-4GlcNAc-Manα1/3; Galβ1-4GlcNAc; Fucα1→6 |
| 20 | 3001 | Galβ1-4GlcNAc-Galβ1-4GlcNAc\Galβ1-4GlcNAc-Manα1\6→Manβ1-4GlcNAcβ1-4GlcNAc-2-AA; Galβ1-4GlcNAc-Manα1/3; Galβ1-4GlcNAc; Fucα1→6 |

TABLE 3

| Peak No. | MW | Structure |
|---|---|---|
| 21 | 1557 | Man-Manα1\6<br>               Manβ1-4GlcNAcβ1-4GlcNAc-2-AA<br>Galβ1-4GlcNAc-Manα1/3 |
| 22 | 1598 | GlcNAc-Manα1\6<br>             Manβ1-4GlcNAcβ1-4GlcNAc-2-AA<br>Galβ1-4GlcNAc-Manα1/3 |
| 23 | 1743 | GlcNAc-Manα1\6<br>             Manβ1-4GlcNAcβ1-4GlcNAc-2-AA<br>Galβ1-4GlcNAc-Manα1/3               6<br>                                                   Fucα1 |
| 24 | 2270 | Galβ1-4GlcNAc\<br>Galβ1-4GlcNAc-Manα1\6<br>               Manβ1-4GlcNAcβ1-4GlcNAc-2-AA<br>Galβ1-4GlcNAc-Manα1/3      6<br>                                   Fucα1 |
| 25 | 2417 | Galβ1-4GlcNAc\<br>Galβ1-4GlcNAc-Manα1\6<br>               Manβ1-4GlcNAcβ1-4GlcNAc-2-AA<br>Galβ1-4GlcNAc-Manα1/3      6<br>       3                     Fucα1<br>   Fucα1 |
| 26 | 2491 | Galβ1-4GlcNAc\<br>Galβ1-4GlcNAc-Manα1\6<br>               Manβ1-4GlcNAcβ1-4GlcNAc-2-AA<br>Galβ1-4GlcNAc-Manα1/3<br>Galβ1-4GlcNAc/ |
| 27 | 2563 | Fucα1<br>  3<br>Galβ1-4GlcNAc\<br>Galβ1-4GlcNAc-Manα1\6<br>               Manβ1-4GlcNAcβ1-4GlcNAc-2-AA<br>Galβ1-4GlcNAc-Manα1/3      6<br>   3                    Fucα1<br>Fucα1 |
| 28 | 2782 | Galβ1-4GlcNAc\<br>Galβ1-4GlcNAc-Manα1\6<br>               Manβ1-4GlcNAcβ1-4GlcNAc-2-AA<br>Galβ1-4GlcNAc-Manα1/3      6<br>Galβ1-4GlcNAc/          Fucα1<br>  3<br>Fucα1 |

TABLE 4

| Peak No. | MW | Structure |
|---|---|---|
| 29 | 2928 | Fucα1↓3<br>Galβ1-4GlcNAc<br>Galβ1-4GlcNAc-Manα1\\_6<br>　　　　　　　　　　　Manβ1-4GlcNAcβ1-4GlcNAc-2-AA<br>Galβ1-4GlcNAc-Manα1/ 3　　　　6<br>Galβ1-4GlcNAc/　　　　　　　Fucα1<br>　　　3<br>　　Fucα1 |
| 30 | 3147 | Galβ1-4GlcNAc-Galβ1-4GlcNAc\\<br>　　　　Galβ1-4GlcNAc-Manα1\\_6<br>　　　　　　　　　　　　Manβ1-4GlcNAcβ1-4GlcNAc-2-AA<br>　　　　Galβ1-4GlcNAc-Manα1/ 3　　　　6<br>　　　　Galβ1-4GlcNAc/　　　　　　　Fucα1<br>　　　　3<br>　　Fucα1 |
| 31 | 3366 | Galβ1-4GlcNAc-Galβ1-4GlcNAc\\<br>Galβ1-4GlcNAc-Galβ1-4GlcNAc-Manα1\\_6<br>　　　　　　　　　　　　Manβ1-4GlcNAcβ1-4GlcNAc-2-AA<br>　　　　Galβ1-4GlcNAc-Manα1/ 3　　　　6<br>　　　　Galβ1-4GlcNAc/　　　　　　　Fucα1 |
| 32 | 1921 | Man\\<br>Galβ1-4GlcNAc-Manα1\\_6<br>　　　　　　　　Manβ1-4GlcNAcβ1-4GlcNAc-2-AA<br>Galβ1-4GlcNAc-Manα1/ 3　　6<br>　　　　　　　　　　Fucα1 |
| 33 | 2109 | Galβ1-4GlcNAc-Manα1\\_6<br>　　　　　　　　Manβ1-4GlcNAcβ1-4GlcNAc-2-AA<br>Galβ1-4GlcNAc-Manα1/ 3 4　　6<br>　　　　　GlcNAcα1　Fucα1 |
| 34 | 3731 | (Galβ1-4GlcNAc)₂-Galβ1-4GlcNAc\\<br>　　Galβ1-4GlcNAc-Galβ1-4GlcNAc-Manα1\\_6<br>　　　　　　　　　　　　Manβ1-4GlcNAcβ1-4GlcNAc-2-AA<br>　　　　Galβ1-4GlcNAc-Manα1/ 3　　　　6<br>　　　　Galβ1-4GlcNAc/　　　　　　　Fucα1 |

TABLE 5

| Peak No. | MW | Structure |
|---|---|---|
| 35 | 4096 | (Galβ1-4GlcNAc)₂-Galβ1-4GlcNAc\\<br>　Galβ1-4GlcNAc-Galβ1-4GlcNAc-Manα1\\_6<br>　　　　　　　　　　　　Manβ1-4GlcNAcβ1-4GlcNAc-2-AA<br>　Galβ1-4GlcNAc-Galβ1-4GlcNAc-Manα1/ 3　　6<br>　　　　Galβ1-4GlcNAc/　　　　　　　Fucα1 |

TABLE 5-continued

| Peak No. | MW | Structure |
|---|---|---|
| 36 | 4461 | (Galβ1-4GlcNAc)$_2$-Galβ1-4GlcNAc\\<br>(Galβ1-4GlcNAc)$_2$-Galβ1-4GlcNAc-Manα1$\diagdown^6$<br>$\phantom{xxxxxxxxxxxxxxxxxxxxxxxx}_3$Manβ1-4GlcNAcβ1-4GlcNAc-2-AA<br>Galβ1-4GlcNAc-Galβ1-4GlcNAc-Manα1$\diagup$ $\phantom{xx}|^6$<br>Galβ1-4GlcNAc$\diagup$ $\phantom{xxxxxxxxxxxxxxxxxxxxx}$Fucα1 |
| 37 | 4826 | (Galβ1-4GlcNAc)$_3$-Galβ1-4GlcNAc\\<br>(Galβ1-4GlcNAc)$_2$-Galβ1-4GlcNAc-Manα1$\diagdown^6$<br>$\phantom{xxxxxxxxxxxxxxxxxxxxxxxx}_3$Manβ1-4GlcNAcβ1-4GlcNAc-2-AA<br>Galβ1-4GlcNAc-Galβ1-4GlcNAc-Manα1$\diagup$ $\phantom{xx}|^6$<br>Galβ1-4GlcNAc$\diagup$ $\phantom{xxxxxxxxxxxxxxxxxxxxx}$Fucα1 |
| 38 | 5191 | (Galβ1-4GlcNAc)$_3$-Galβ1-4GlcNAc\\<br>(Galβ1-4GlcNAc)$_2$-Galβ1-4GlcNAc-Manα1$\diagdown^6$<br>$\phantom{xxxxxxxxxxxxxxxxxxxxxxxx}_3$Manβ1-4GlcNAcβ1-4GlcNAc-2-AA<br>Galβ1-4GlcNAc-Galβ1-4GlcNAc-Manα1$\diagup$ $\phantom{xx}|^6$<br>Galβ1-4GlcNAc-Galβ1-4GlcNAc$\diagup$ $\phantom{xxxxxxxxxxxxxx}$Fucα1 |
| 39 | 5556 | (Galβ1-4GlcNAc)$_3$-Galβ1-4GlcNAc\\<br>(Galβ1-4GlcNAc)$_2$-Galβ1-4GlcNAc-Manα1$\diagdown^6$<br>$\phantom{xxxxxxxxxxxxxxxxxxxxxxxx}_3$Manβ1-4GlcNAcβ1-4GlcNAc-2-AA<br>(Galβ1-4GlcNAc)$_2$-Galβ1-4GlcNAc-Manα1$\diagup$ $\phantom{xx}|^6$<br>Galβ1-4GlcNAc-Galβ1-4GlcNAc$\diagup$ $\phantom{xxxxxxxxxxxxxx}$Fucα1 |
| 40 | 2474 | Galβ1-4GlcNAc-Manα1$\diagdown^6$<br>$\phantom{xxxxxxxxxxxxxx}_3$Manβ1-4GlcNAcβ1-4GlcNAc-2-AA<br>Galβ1-4GlcNAc-Manα1$\diagup^{\phantom{x}4}$ $\phantom{xx}|^6$<br>Galβ1-4GlcNAc$\diagup$ GlcNAcα1 $\phantom{xx}$Fucα1 |

Example 4

Free Oligosaccharide 1 Present in Cells

Human gastric cancer cells MKN 45 were washed with PBS and homogenized with a glass homogenizer in 10 mM Na$_2$HPO$_4$ (pH 7.5) containing 1% protease inhibitor to a concentration of 1×10$^8$ cells/5 ml, 10 ml of 20 mM Tris-HCl buffer (pH 7.5) containing 0.5 M sucrose was then added to the mixture, the resulting mixture was centrifuged at 3000 rpm, 4° C. for 15 minutes, and the supernatant was thereafter collected and centrifuged at 19000 rpm, 4° C. The resulting supernatant was treated in a vacuum to dryness to obtain a free-type oligosaccharide mixture.

In the same manner as in Example 1, 2-AA was introduced into the oligosaccharide mixture to obtain a mixture of free-type oligosaccharides, which was fractionated by serotonin affinity column chromatography to obtain free-type oligosaccharide derivatives.

Figure 8:
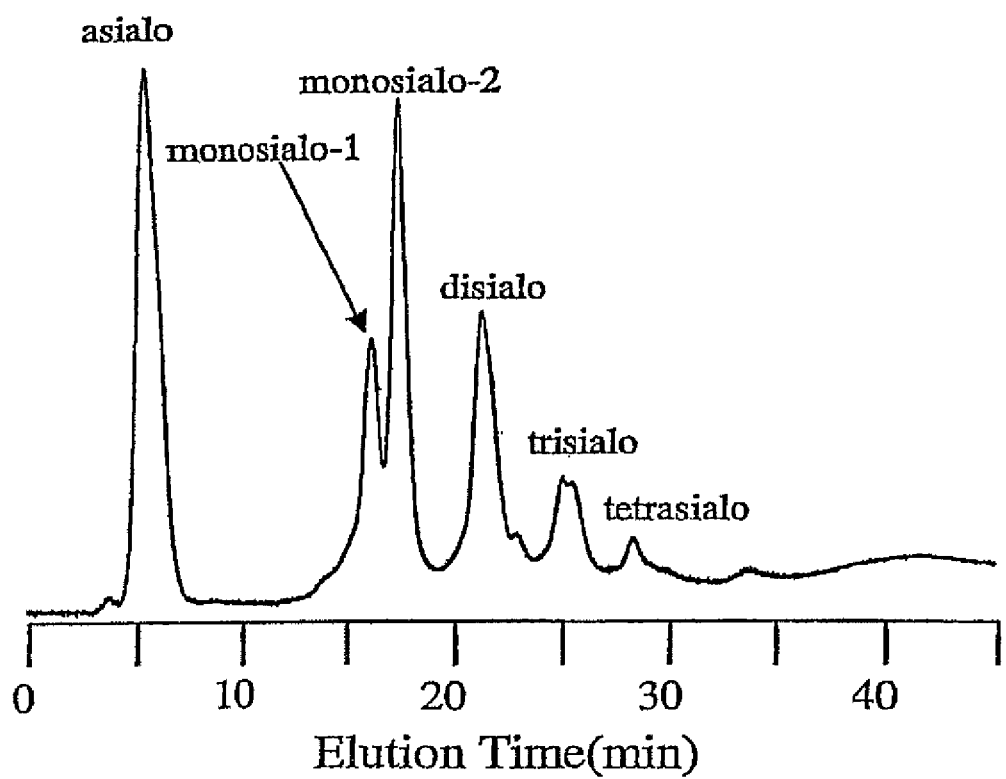
FIG. 8 is of oligosaccharide derivatives obtained in Example 4.
Figure 9:
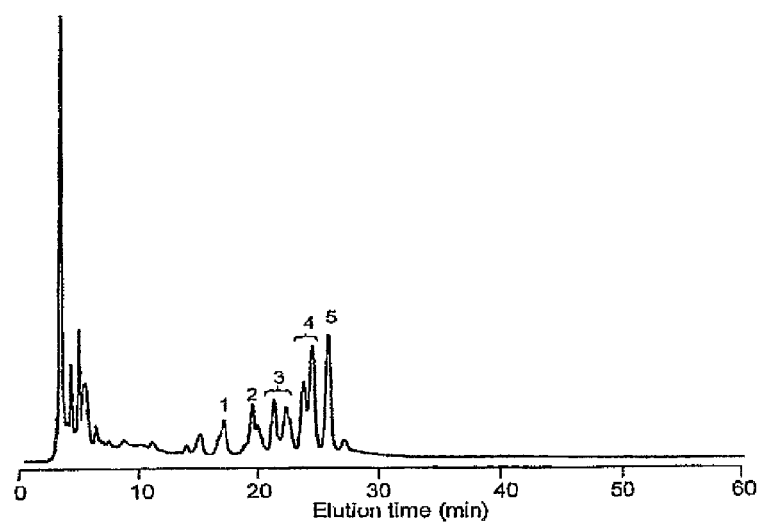
FIG. 9 is a chromatogram of HPLC of oligosaccharide derivatives obtained in Example 5.

FIG. 8 shows the result of separation by the affinity column chromatography. Each fraction obtained was separated by normal phase HPLC using an amino column to obtain a free-type oligosaccharide derivative.
Conditions for HPLC
Column: Asahi Shodex NH2P-50 4E (Showa Denko, Tokyo, Japan, 4.6×250 mm)
Column temperature: 50° C.
Pump: JASCO Model PU-980
Flow rate: 1 ml/min
Detector: JASCO Model FP-920 fluorescent detector
Excitation wavelength: 350 nm
Fluorescent wavelength: 425 nm
Mobile phase: acetonitrile solution containing 2% acetic acid and serving as solution A and aqueous solution containing 5% of acetic acid and 3% of triethylamine and used as solution B
Gradient conditions: Linear gradient elution was conducted using 30% of solution B for 2 minutes after the sample was poured in so that the amount of solution B would be 95% in 80 minutes. Solution B was maintained in an amount of 95% for 100 minutes.

The free-type oligosaccharide derivative obtained was suitably treated with glycosidase (sialidase, α-mannosidase, β-galactosidase, β-acetylhexaminidase, etc.), followed by normal phase HPLC for separation using the above-mentioned amino column. The fractions obtained were lyophilized and analyzed by MALDI-TOF MS to determine the structure of the oligosaccharide derivative.

The treatment with α-mannosidase is conducted by dissolving the oligosaccharide derivative in 20 μl of 20 mM citric acid buffer (pH 4.5), adding 2 μl of α-mannosidase (10 mM, product of Seikagaku Kogyo Co., Ltd.), reacting the mixture at 37° C. for 24 hours, boiling the reaction mixture at 100° C. for 3 minutes, centrifuging the mixture and collecting the supernatant. The treatment with the other hydrolases were conducted in the same manner as in the foregoing example. Tables 6 and 7 show the oligosaccharide derivatives obtained.

The free oligosaccharides given in Tables 6 and 7 are novel compounds. For example, oligosaccharide derivative No. 1 which is 1321 in molecular weight is represented by the formula given below.

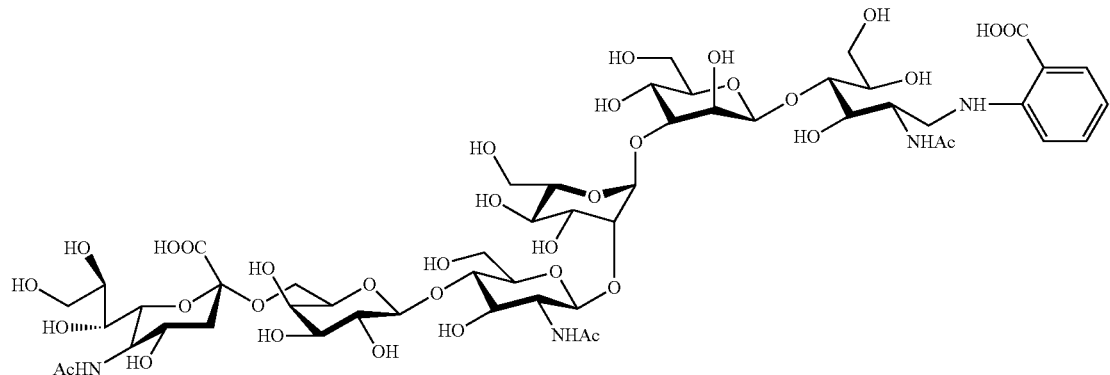

TABLE 6

| MW | Structure |
|---|---|
| 1321 | NeuAc-Galβ1-4GlcNAc-Manα1-3Manβ1-4GlcNAc-2-AA |
| 1483 | Manα1-6 / NeuAc-Galβ1-4GlcNAc-Manα1-3 Manβ1-4GlcNAc-2-AA |
| 1686 | GlcNAc-Manα1-6 / NeuAc-Galβ1-4GlcNAc-Manα1-3 Manβ1-4GlcNAc-2-AA |
| 2140 | NeuAc-Galβ1-4GlcNAc-Manα1-6 / NeuAc-Galβ1-4GlcNAc-Manα1-3 Manβ1-4GlcNAc-2-AA |
| 2343 | GlcNAc \ NeuAc-Galβ1-4GlcNAc-Manα1-6 / NeuAc-Galβ1-4GlcNAc-Manα1-3 Manβ1-4GlcNAc-2-AA / NeuAc-Galβ1-4GlcNAc |

TABLE 6-continued

| MW | Structure |
|---|---|
| 2505 | (NeuAc⁻)₂ { Galβ1-4GlcNAc \ Galβ1-4GlcNAc-Manα1-6 / Manβ1-4GlcNAc-2-AA / Galβ1-4GlcNAc-Manα1-3 } |
| 2795 | NeuAc-Galβ1-4GlcNAc \ NeuAc-Galβ1-4GlcNAc-Manα1-6 / Manβ1-4GlcNAc-2-AA / NeuAc-Galβ1-4GlcNAc-Manα1-3 |
| 2999 | (NeuAc⁻)₃ { GlcNAc \ Galβ1-4GlcNAc-Manα1-6 / Manβ1-4GlcNAc-2-AA / Galβ1-4GlcNAc-Manα1-3 / Galβ1-4GlcNAc } |
| 3160 | (NeuAc⁻)₃ { Galβ1-4GlcNAc \ Galβ1-4GlcNAc-Manα1-6 / Manβ1-4GlcNAc-2-AA / Galβ1-4GlcNAc-Manα1-3 / Galβ1-4GlcNAc } |

TABLE 7

| MW | Structure |
|---|---|
| 3451 | NeuAc-Galβ1-4GlcNAc \ NeuAc-Galβ1-4GlcNAc-Manα1-6 / Manβ1-4GlcNAc-2-AA / NeuAc-Galβ1-4GlcNAc-Manα1-3 / NeuAc-Galβ1-4GlcNAc |

TABLE 7-continued

| MW | Structure |
|---|---|
| 3816 | NeuAc-Galβ1-4GlcNAc-Galβ1-4GlcNAc<br>                                  \\<br>          NeuAc-Galβ1-4GlcNAc-Manα1<br>                                    6<br>                                        Manβ1-4GlcNAc-2-AA<br>                                      3<br>          NeuAc-Galβ1-4GlcNAc-Manα1<br>                                /<br>            NeuAc-Galβ1-4GlcNAc |

Example 5

A mixture of free-type oligosaccharides was obtained by the same procedure as in Example 4 with the exception of using human T cell lymphoma Jurkat 27 (oligosaccharide-introduced cell strain) in place of human gastric cancer cells MKN45.

In the same manner as in Example 1, 2-AA was introduced into the free-type oligosaccharide mixture obtained to prepare a mixture of free-type oligosaccharide derivatives, which was fractionated by serotonin column chromatography to obtain free-type oligosaccharide derivatives Each fraction obtained was separated by normal phase HPLC using an amide column to obtain a free-type oligosaccharide derivative.

Conditions for HPLC

Column: TSK-GEL Amide-80 (TOSOH CORPORATION, Japan, 4.6×250 mm)

Column temperature: 40° C.

Pump: JASCO Model PU-980

Flow rate: 1 ml/min

Detector: JASCO Model FP-920 fluorescent detector

Excitation wavelength: 350 nm

Fluorescent wavelength: 425 nm

Mobile phase: acetonitrile solution containing 0.1% acetic acid and serving as solution A and aqueous solution containing 0.2% of acetic acid and 0.2% of triethylamine and used as solution B Gradient conditions: Linear gradient elution was conducted using 30% of solution B for 2 minutes after the sample was poured in so that the amount of solution B would be 65% in 60 minutes.

The free-type oligosaccharide derivatives obtained were analyzed by the same procedure as in Example 4 to determine the structure. Table 8 shows the oligosaccharide derivatives obtained.

TABLE 8

| Peak No. | Structure |
|---|---|
| 1 | Man\\<br>   Man-Man\\<br>            Man-GlcNAc-2-AA<br>   Man/ |
| 2 | Man\\<br>   Man-Man\\<br>            Man-GlcNAc-2-AA<br>   Man-Man/ |
| 3 | Man⁻ { Man\\ , Man-Man\\ , Man-Man/ } Man-GlcNAc-2-AA |
| 4 | (Man⁻)₂ { Man\\ , Man-Man\\ , Man-Man/ } Man-GlcNAc-2-AA |
| 5 | Man-Man\\<br>Man-Man-Man\\<br>                Man-GlcNAc-2-AA<br>Man-Man-Man/ |

Example 6

Oligosaccharides of Human Cervical Cancer Cells

Human cervical cancer cells HeLa were incubated using DMEM containing 10% of NCS immobilized in advance by being heated at 50° C. for 30 minutes. In 80% confluent state, the cells being incubated were washed with PBS and then treated at 37° C. for 5 minutes with addition of a trypsin solution, and the cells separated were collected, washed with PBS and thereafter subcultured. The same procedures as in Example 2 were repeated for the preparation of a cell membrane fraction and separation of oligosaccharides from the cell membrane fraction to obtain an oligosaccharide mixture derived from cell membranes. In the same manner as in Example 1, 2-AA was introduced into the mixture, followed by serotonin affinity chromatography to obtain oligosaccharide derivative fractions.

Figure 10:
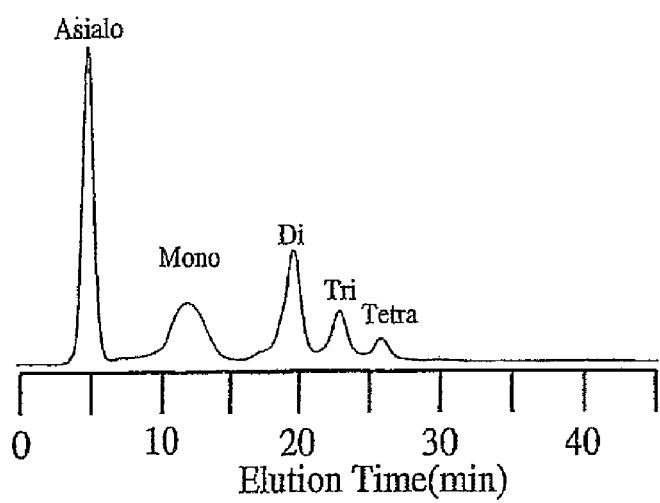
FIG. 10 is an affinity column chromatogram of oligosaccharide derivatives obtained in Example 6.

FIG. 10 shows the result of separation by the column chromatography.

The asialo oligosaccharide derivative fraction, monosialo oligosaccharide derivative fraction and disialo oligosaccharide derivative fraction were treated with sialidase and thereafter subjected to normal phase HPLC using an amino column for separation to obtain oligosaccharide derivatives The same conditions as in Example 4 were used for HPLC.

The oligosaccharide derivatives obtained were suitably treated with glycosidase (sialidase, α-mannosidase, β-galactosidase, β-acetylhexaminidase, etc.), followed by normal phase HPLC for separation using the above-mentioned amino column. The fractions obtained were lyophilized and thereafter analyzed by MALDI-TOF MS to determine the structure of the oligosaccharide derivatives.

Tables 9 to 12 show the oligosaccharide derivatives obtained.

TABLE 9 asialo oligosaccharide derivative

| MW | Structure |
|---|---|
| 1354 | Man\Man-Manα1\₆Manβ1-4GlcNAcβ1-4GlcNAc-2-AA / Manα1⌐³ |
| 1516 | Man\Man-Manα1\₆Manβ1-4GlcNAcβ1-4GlcNAc-2-AA / Man-Manα1⌐³ |
| 1678 | Man-Man\Man-Manα1\₆Manβ1-4GlcNAcβ1-4GlcNAc-2-AA / Man-Manα1⌐³ |
| 1760 | Galβ1-4GlcNAc-Manα1\₆Manβ1-4GlcNAcβ1-4GlcNAc-2-AA / Galβ1-4GlcNAc-Manα1⌐³ |
| 1840 | Man\Man-Man-Manα1\₆Manβ1-4GlcNAcβ1-4GlcNAc-2-AA / Man-Man-Manα1⌐³ |
| 1906 | Galβ1-4GlcNAc-Manα1\₆Manβ1-4GlcNAcβ1-4GlcNAc-2-AA / Galβ1-4GlcNAc-Manα1⌐³ ; Fucα1 on 6 |
| 2002 | Man-Man\Man-Manα1\₆Manβ1-4GlcNAcβ1-4GlcNAc-2-AA / Man-Manα1⌐³ |

TABLE 10 monosialo oligosaccharide derivative

| MW | Structure |
|---|---|
| 1686 | NeuAc-Galβ1-4GlcNAc-Manα1\₆Manβ1-4GlcNAcβ1-4GlcNAc-2-AA / Manα1⌐³ |
| 1889 | NeuAc-Galβ1-4GlcNAc-Manα1\₆Manβ1-4GlcNAcβ1-4GlcNAc-2-AA / Manα1⌐³ ; GlcNAcα1 on 4 |
| 2051 | NeuAc⁻{ Galβ1-4GlcNAc-Manα1\₆Manβ1-4GlcNAcβ1-4GlcNAc-2-AA / Galβ1-4GlcNAc-Manα1⌐³ } |
| 2197 | NeuAc⁻{ Galβ1-4GlcNAc-Manα1\₆Manβ1-4GlcNAcβ1-4GlcNAc-2-AA / Galβ1-4GlcNAc-Manα1⌐³ } ; Fucα1 on 6 |
| 2254 | NeuAc⁻{ Galβ1-4GlcNAc-Manα1\₆Manβ1-4GlcNAcβ1-4GlcNAc-2-AA / Galβ1-4GlcNAc-Manα1⌐³ } ; GlcNAcα1 on 4 |
| 2343 | NeuAc⁻{ Galβ1-4GlcNAc-Manα1\₆Manβ1-4GlcNAcβ1-4GlcNAc-2-AA / Galβ1-4GlcNAc-Manα1⌐³ } ; Fucα1 on 3 of lower branch; Fucα1 on 6 |

TABLE 10-continued monosialo oligosaccharide derivative

| MW | Structure |
|---|---|
| 2400 | NeuAc⁻ { Galβ1-4GlcNAc-Manα1→6 \ Galβ1-4GlcNAc-Manα1→3 / Manβ1-4GlcNAcβ1-4GlcNAc-2-AA; 4-GlcNAcα1; 6-Fucα1 } |
| 2546 | NeuAc⁻ { Galβ1-4GlcNAc-Manα1→6 \ Galβ1-4GlcNAc-Manα1(3-Fucα1)→3 / Manβ1-4GlcNAcβ1-4GlcNAc-2-AA; 4-GlcNAcα1; 6-Fucα1 } |

TABLE 11 disialo oligosaccharide derivative-1

| MW | Structure |
|---|---|
| 2342 | NeuAc-Gal-GlcNAc-Manα1→6 \ NeuAc-Gal-GlcNAc-Manα1→3 / Manβ1-4GlcNAcβ1-4GlcNAc-2-AA |
| 2545 | (NeuAc⁻)₂ { Gal-GlcNAc-Manα1→6 \ Gal-GlcNAc-Manα1→3 / Manβ1-4GlcNAcβ1-4GlcNAc-2-AA; 4-GlcNAcα1 } |
| 2691 | (NeuAc⁻)₂ { Gal-GlcNAc-Manα1→6 \ Gal-GlcNAc-Manα1→3 / Manβ1-4GlcNAcβ1-4GlcNAc-2-AA; 4-GlcNAcα1; 6-Fucα1 } |
| 2748 | (NeuAc⁻)₂ { GlcNAc \ Gal-GlcNAc-Manα1→6 \ Gal-GlcNAc-Manα1→3 / Manβ1-4GlcNAcβ1-4GlcNAc-2-AA; 4-GlcNAcα1 } |
| 2894 | (NeuAc⁻)₂ { GlcNAc \ Gal-GlcNAc-Manα1→6 \ Gal-GlcNAc-Manα1→3 / Manβ1-4GlcNAcβ1-4GlcNAc-2-AA; 4-GlcNAcα1; 6-Fucα1 } |
| 3056 | (NeuAc⁻)₂ { Gal-GlcNAc-Manα1→6 \ Gal-GlcNAc-Manα1→3 / Manβ1-4GlcNAcβ1-4GlcNAc-2-AA; Gal-GlcNAc; GlcNAcα1; Fucα1 } |
| 3113 | (NeuAc⁻)₂ { GlcNAc-Gal-GlcNAc \ Gal-GlcNAc-Manα1→6 \ Gal-GlcNAc-Manα1→3 / Manβ1-4GlcNAcβ1-4GlcNAc-2-AA; GlcNAcα1 } |

TABLE 12 disialo oligosaccharide derivative-2

| MW | Structure |
|---|---|
| 3259 | (NeuAc⁻)₂ { GlcNAc-Gal-GlcNAc\Gal-GlcNAc-Manα1⁶\₃Manβ1-4GlcNAcβ1-4GlcNAc-2-AA ; Gal-GlcNAc-Manα1 — 4 — 6 ; GlcNAcα1 ; Fucα1 } |
| 3405 | (NeuAc⁻)₂ { GlcNAc-Gal-GlcNAc\Gal-GlcNAc-Manα1⁶\₃Manβ1-4GlcNAcβ1-4GlcNAc-2-AA ; Gal-GlcNAc-Manα1 — 4 — 6 ; ³GlcNAcα1 ; Fucα1 ; Fucα1 } |
| 3421 | (NeuAc⁻)₂ { GlcNAc-Gal-GlcNAc\Gal-GlcNAc-Manα1⁶\₃Manβ1-4GlcNAcβ1-4GlcNAc-2-AA ; Gal-GlcNAc-Manα1 ; Gal-Glc-NAc — 6 ; Fucα1 } |
| 3624 | (NeuAc⁻)₂ { GlcNAc-Gal-GlcNAc\Gal-GlcNAc-Manα1⁶\₃Manβ1-4GlcNAcβ1-4GlcNAc-2-AA ; Gal-GlcNAc-Manα1 — 4 — 6 ; Gal-Glc-NAc / GlcNAcα1 ; Fucα1 } |

Example 7

Oligosaccharides of Cancer Cell-Specific Antigen CD98

Preparation of CD98-HC by Immune Sedimentation

Protein A-Agarose (50 µl, product of Sigma-Aldrich Japan) was washed with 200 µl of PBS. 50 µl of PBS and 10 µg/10 µl of anti-CD 98 antibody were added to the agarose, and the mixture was reacted at room temperature for 60 minutes. The resation mixture was washed with 1 ml of PBS to remove the unadsorbed component to obtain Agarose having anti-CD98 antibody immobilized thereon. To the agarose was added a membrane fraction ($2 \times 10^7$ cells) of HeLa cells solubilized with 400 µl of 1% NP-40, and the mixture was incubated overnight at 4° C. using a rotary shaker. The culture was washed with 1 ml of PBS, the unadsorbed component was removed, followed by centrifuging. To the agarose having anti-CD98 antibody immobilized thereon was added 20 µl of a 9:1 mixture of dissociation solution (250 mM Tris-HCl buffer pH 6.8/4.6% SDS, 20% glycerin) and 2-mercaptoethyl alcohol, the mixture was boiled for 5 minutes and centrifuged at 15000 rpm, and the supernatant was taken as CD98-HC and subjected to PAGE.

SDS Polyacrylamide Gel Electrophoresis

The gel electrophoresis device and power source used were products of Bio Rad. The electrophoresis was conducted using 7.5% gel and a buffer of 25 mM Tris, 198 mM glycine and 1% (w/v) SDS, at 5 mA per sheet of gel for the first 1 hour and subsequently at 10 mA to the lower side portion of the gel.

Coomassie Brilliant Blue Staining

After SDS-PAGE, proteins were stained in a solution of 40% (v/w) methanol, 10% (v/w) acetic acid/0.2% Coomassie Brilliant Blue R-250. One hour later, the proteins were decolored with a mixture of methanol, acetic acid and water (4:1:5)

Western Blot

The protein sample in the gel resulting from SDS-PAGE was transferred onto the PVDF membrane using Semi-Dry Blotting Device (Trans-Blot SD cell, product of BIO-RAD). Before use, the PVDF membrane was immersed in methanol for 60 seconds and thereafter immersed in 48 mM Tris, 39 mM glycine, 20% methanol (pH 9.0) for 1 hour. The transfer was conducted with the application of voltage for 1 hour at a constant current of 100 mA. After the transfer, a blocking procedure was performed for the PVDF membrane using PBS containing 5% skim milk and 0.05% Tween 20, and 0.05% Tween 20/PBS (5 ml) containing 5 µg of anti-CD98 antibody was thereafter added to the membrane, followed by a reaction overnight. After the reaction, the PVDF membrane was washed four times with PBS (20 ml) containing 0.05% Tween 20. Subsequently added to the membrane was 5 ml of 0.05% Tween 20/PBS mixture containing 5 µl of HRP-labeled Protein A, followed by a reaction for 1 hour. The PVDF membrane was then washed four times with PBS (20 ml) containing 0.05% Tween 20. To the membrane were then added 20 ml of 0.0031% hydrogen peroxide solution (100 mM Tris-HCl buffer 7.5 in pH) and containing 0.05% DAB (3,3-diaminobennzidrine tetrahydrochloride) for color development.

Intragel Digestion with N-glycanase

After bands were recognized by CBB staining, the discolored solution was replaced by water, and desired bands were cut out and placed into an Eppendorf tube. With addition of 100 μl of acetonitrile, the tube was then allowed to stand for 30 minutes to thereby remove water from the gel. After the removal of the acetonitrile, 100 μl of Trsi-HCl buffer 7.5 in pH and containing 2 units of N-glycanase F was placed in, the mixture was incubated overnight at 37° C., and oligosaccharides were cut out. Subsequently, the extract was collected, 200 μl of water was added thereto, the mixture was stirred for 30 minutes, and an oligosaccharide mixture was obtained from the gel.

In the manner as in Example 1, 2-AA was introduced into the oligosaccharide mixture thus obtained, and the resulting mixture was treated by serotonin affinity column chromatography to collect fractions of oligosaccharides.

Figure 11:
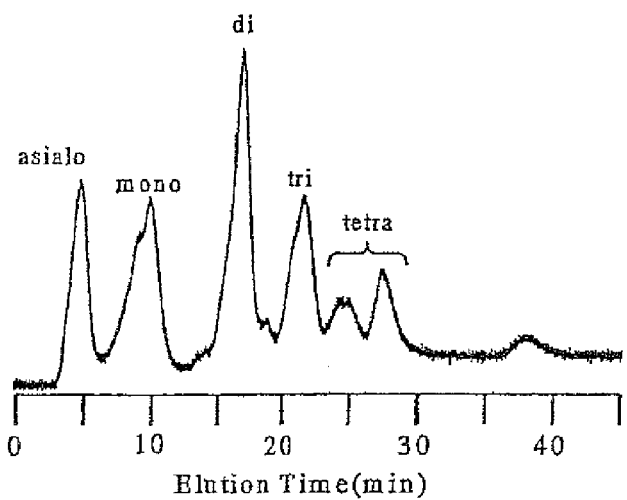
FIG. 11 is an affinity column chromatogram of oligosaccharide derivatives obtained in Example 7.

FIG. 11 shows the result of separation by the column chromatography.

Figure 12:
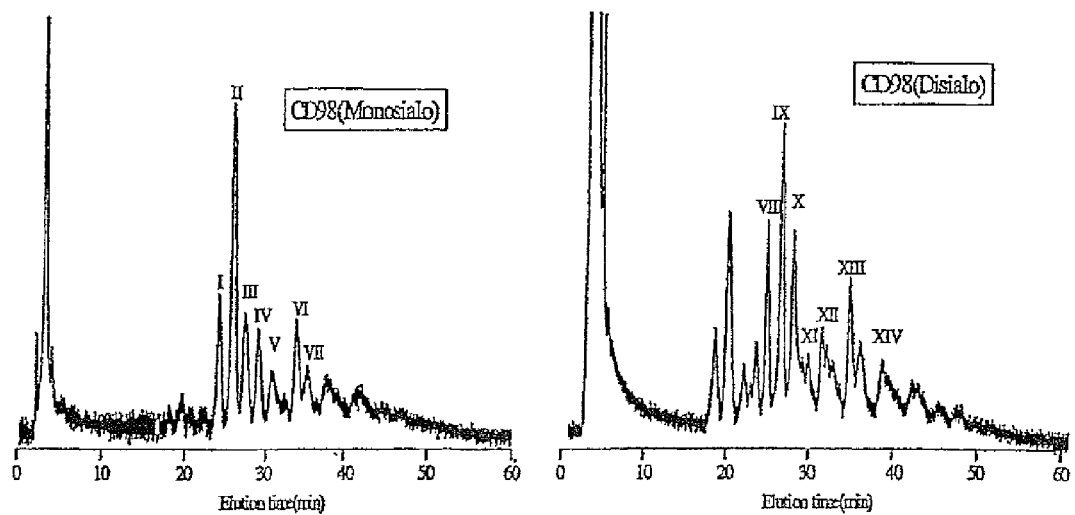
FIG. 12 are chromatograms of HPLC of oligosaccharide derivatives obtained in Example 7.

The monosialo oligosaccharide derivative fraction and the disialo oligosaccharide derivative fraction obtained were treated with sialidase and thereafter treated by normal phase HPLC using an amino column to obtain oligosaccharide derivatives. The same conditions as in Example 4 were used for HPLC. FIG. 12 shows the result of separation by HPLC.

The oligosaccharide derivatives obtained were suitably treated with glycosidase (sialidase, α-mannosidase, β-galactosidase, β-acetylhexaminidase, etc.), followed by normal phase HPLC for separation using the above-mentioned amino column. The fractions obtained were lyophilized and thereafter analyzed by MALDI-TOF MS to determine the structure of the oligosaccharide derivatives.

Tables 13 and 14 show the oligosaccharide derivatives obtained.

TABLE 13

| Peak No. | MW | Structure |
|---|---|---|
| I | 2051 | NeuAc⁻ { Galβ1-4GlcNAc-Manα1⁶ ₃Manβ1-4GlcNAcβ1-4GlcNAc-2-AA / Galβ1-4GlcNAc-Manα1 } |
| II | 2197 | NeuAc⁻ { Galβ1-4GlcNAc-Manα1⁶ ₃Manβ1-4GlcNAcβ1-4GlcNAc-2-AA / Galβ1-4GlcNAc-Manα1 } with Fucα1 at 6 position |
| III | 2343 | NeuAc⁻ { Galβ1-4GlcNAc-Manα1⁶ ₃Manβ1-4GlcNAcβ1-4GlcNAc-2-AA / Galβ1-4GlcNAc-Manα1 (³Fucα1) } with Fucα1 at 6 position |
| IV | 2400 | NeuAc⁻ { Galβ1-4GlcNAc-Manα1⁶ ₃,⁴Manβ1-4GlcNAcβ1-4GlcNAc-2-AA / Galβ1-4GlcNAc-Manα1, GlcNAcα1 } with Fucα1 at 6 position |
| V | 2562 | NeuAc⁻ { Galβ1-4GlcNAc\Galβ1-4GlcNAc-Manα1⁶ ₃Manβ1-4GlcNAcβ1-4GlcNAc-2-AA / Galβ1-4GlcNAc-Manα1 } with Fucα1 at 6 position |
| VI | 2781 | NeuAc⁻ { Galβ1-4GlcNAc\Galβ1-4GlcNAc-Manα1⁶ ₃Manβ1-4GlcNAcβ1-4GlcNAc-2-AA / Galβ1-4GlcNAc-Manα1/Galβ1-4GlcNAc } |

TABLE 13-continued

| Peak No. | MW | Structure |
|---|---|---|
| VII | 2927 | NeuAc⁻ { Galβ1-4GlcNAc, Galβ1-4GlcNAc-Manα1 \⁶ Manβ1-4GlcNAcβ1-4GlcNAc-2-AA ; Galβ1-4GlcNAc-Manα1 /³ ⁶| Fucα1 ; Galβ1-4GlcNAc } |

TABLE 14

| Peak No. | MW | Structure |
|---|---|---|
| VIII | 2342 | NeuAc-Galβ1-4GlcNAc-Manα1 \⁶ Manβ1-4GlcNAcβ1-4GlcNAc-2-AA ; NeuAc-Galβ1-4GlcNAc-Manα1 /³ |
| IX | 2488 | NeuAc-Galβ1-4GlcNAc-Manα1 \⁶ Manβ1-4GlcNAcβ1-4GlcNAc-2-AA ; NeuAc-Galβ1-4GlcNAc-Manα1 /³ ⁶\|Fucα1 |
| X | 2545 | (NeuAc⁻)₂ { Galβ1-4GlcNAc-Manα1 \⁶ Manβ1-4GlcNAcβ1-4GlcNAc-2-AA ; Galβ1-4GlcNAc-Manα1 /³ ⁴\|GlcNAcα1 } |
| XI | 2691 | (NeuAc⁻)₂ { Galβ1-4GlcNAc-Manα1 \⁶ Manβ1-4GlcNAcβ1-4GlcNAc-2-AA ; Galβ1-4GlcNAc-Manα1 /³ ⁴\|GlcNAcα1 ⁶\|Fucα1 } |
| XII | 2853 | (NeuAc⁻)₂ { Galβ1-4GlcNAc, Galβ1-4GlcNAc-Manα1 \⁶ Manβ1-4GlcNAcβ1-4GlcNAc-2-AA ; Galβ1-4GlcNAc-Manα1 /³ ⁶\|Fucα1 } |
| XIII | 3072 | (NeuAc⁻)₂ { Galβ1-4GlcNAc, Galβ1-4GlcNAc-Manα1 \⁶ Manβ1-4GlcNAcβ1-4GlcNAc-2-AA ; Galβ1-4GlcNAc-Manα1 /³ ; Galβ1-4GlcNAc } |
| XIV | 3275 | (NeuAc⁻)₂ { GlcNAc-Galβ1-4GlcNAc, Galβ1-4GlcNAc-Manα1 \⁶ Manβ1-4GlcNAcβ1-4GlcNAc-2-AA ; Galβ1-4GlcNAc-Manα1 /³ ; Galβ1-4GlcNAc } |

INDUSTRIAL APPLICABILITY

Oligosaccharide mixtures in cells and tissues can be meticulously separated and the structure of oligosaccharides can be comprehensively analyzed by the processes of the invention. This serves to explore the oligosaccharides and functions thereof which still remain to be clarified. The invention is therefore expected to contribute a great deal to the research on oligosaccharides in the future.

The invention claimed is:

1. A method of analyzing the structure of an oligosaccharide derived from cancer cells in an oligosaccharide mixture containing sialo oligosaccharides, comprising the steps of
   (a) introducing a lipophilic group to oligosaccharides in the mixture to obtain a mixture of oligosaccharide derivatives, wherein the lipophilic group is selected from the group consisting of 2-carboxyphenylamino, 3-carboxyphenylamino, 4-carboxyphenylamino, p-ethoxycarbonylphenylamino, 2-pyridylamino, 9-fluorenylmethoxycarbonyl (Fmoc), tert-butoxycarbonyl (BOC), benzyl, allyl, allyloxycarbonyl, and acetyl;
   (b) treating the lipophilic group-modified oligosaccharide derivative mixture to serotonin affinity column chromatography to obtain fractions each containing oligosaccharide derivatives having the same number of sialic acid(s);
   (c) treating each fraction obtained in step (b) to normal-phase chromatography using an amino column or amide column; and
   (d) analyzing the oligosaccharide derivative contained in each fraction obtained in step (c) by a mass spectrometric method.

2. The method according to claim 1, further comprising, before step (c), a step (b') of treating the resulting eluate with a glycosidase.

3. The method according to claim 1 wherein the mass spectrometric method comprise MALDI-TOF MS.

* * * * *